(12) United States Patent
Suddaby

(10) Patent No.: US 11,317,949 B2
(45) Date of Patent: May 3, 2022

(54) SEGMENTED ALIGNMENT ROD ASSEMBLY

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 161 days.

(21) Appl. No.: 16/802,695

(22) Filed: Feb. 27, 2020

(65) Prior Publication Data

US 2020/0197048 A1 Jun. 25, 2020

Related U.S. Application Data

(63) Continuation-in-part of application No. 15/962,145, filed on Apr. 25, 2018, now Pat. No. 10,624,683.

(51) Int. Cl.
*A61B 17/70* (2006.01)
*A61B 17/88* (2006.01)
(Continued)

(52) U.S. Cl.
CPC ...... *A61B 17/7029* (2013.01); *A61B 17/8869* (2013.01); *A61B 2017/00398* (2013.01); *A61B 2017/681* (2013.01)

(58) Field of Classification Search
CPC .............. A61B 17/705; A61B 17/7041; A61B 17/7023; A61B 17/7053; A61B 17/8869; A61B 17/7011; A61B 17/7019; A61B 17/707; A61B 17/7025; A61B 17/7067; A61B 17/7031; A61B 17/701;
(Continued)

(56) References Cited

U.S. PATENT DOCUMENTS

| 5,290,289 A | 3/1994 | Sanders et al. |
| 5,649,925 A | 7/1997 | Barbera Alacreu |

(Continued)

FOREIGN PATENT DOCUMENTS

| CN | 207150033 U | 3/2018 |
| WO | WO2007/086053 | 8/2007 |

(Continued)

OTHER PUBLICATIONS https://www.medicrea.com/usa/th-lumbar-range-usa/ib3e-tb. "IB3D-TB", last accessed Jul. 16, 2018.
(Continued)

*Primary Examiner* — Eduardo C Robert
(74) *Attorney, Agent, or Firm* — Simpson & Simpson, PLLC; Michael Nicholas Vranjes

(57) ABSTRACT

A segmented rod assembly for aligning a spine including a plurality of vertebrae, including a rod, including a plurality of segments, the plurality of segments having at least a first segment arranged to be connected to a first vertebra of the spine, the first segment including a first body and at least one tang extending from the first body, and a second segment arranged to be connected to a second vertebra of the spine, the second segment including a second body and at least one channel arranged in the second body, wherein the at least tang is operatively arranged to engage the at least one channel, and at least one tensioning member arranged within the plurality of segments, the at least one tensioning member having a first end secured to the first segment and a second end.

20 Claims, 12 Drawing Sheets

(51) Int. Cl.
　　　*A61B 17/00*　　　　(2006.01)
　　　*A61B 17/68*　　　　(2006.01)

(58) Field of Classification Search
　　　CPC ............ A61B 17/7001; A61B 17/7068; A61B
　　　　　　　17/7014; A61B 17/7035; A61B 17/7044;
　　　　　　　　A61B 17/704; A61B 17/7004; A61B
　　　　　　　17/7062; A61B 17/7049; A61B 17/7029;
　　　　　　　　　A61B 2017/681; A61B 2017/00212
　　　USPC ...................................... 606/62–64, 246–279
　　　See application file for complete search history.

(56) References Cited

U.S. PATENT DOCUMENTS

| | | | |
|---|---|---|---|
| 5,879,352 A * | 3/1999 | Filoso | A61B 17/72 |
| | | | 606/62 |
| 6,296,644 B1 | 10/2001 | Saurat et al. | |
| 6,607,530 B1 | 8/2003 | Carl et al. | |
| 7,410,489 B2 | 8/2008 | Dakin et al. | |
| 7,634,874 B2 | 12/2009 | Lucas | |
| 7,658,753 B2 * | 2/2010 | Carl | A61B 17/7064 |
| | | | 606/257 |
| 7,766,941 B2 | 8/2010 | Paul | |
| 7,785,325 B1 | 8/2010 | Milbank | |
| 7,815,665 B2 * | 10/2010 | Jahng | A61B 17/7007 |
| | | | 606/263 |
| 8,057,472 B2 * | 11/2011 | Walker | A61B 17/68 |
| | | | 606/57 |
| 8,105,360 B1 | 1/2012 | Connor | |
| 8,114,133 B2 * | 2/2012 | Logan | A61B 17/7032 |
| | | | 606/258 |
| 8,133,241 B2 | 3/2012 | Boyd et al. | |
| 8,206,423 B2 | 6/2012 | Siegal | |
| 8,353,935 B2 | 1/2013 | Krause | |
| 8,398,633 B2 | 3/2013 | Mueller | |
| 8,685,022 B2 | 4/2014 | Lorenz et al. | |
| 8,709,042 B2 | 4/2014 | Greenbalgh et al. | |
| 8,768,509 B2 | 7/2014 | Unsworth | |
| 8,845,690 B2 | 9/2014 | Capozzoli | |
| 9,050,112 B2 | 6/2015 | Greenhalgh et al. | |
| 9,113,783 B2 | 8/2015 | Suehara | |
| 9,144,506 B2 | 9/2015 | Phelps | |
| 9,221,179 B2 | 12/2015 | Hinman | |
| 9,339,298 B1 | 5/2016 | Morales Chavarria | |
| 9,504,307 B1 | 11/2016 | Burnett et al. | |
| 9,592,132 B2 | 3/2017 | Hauck et al. | |
| 9,642,712 B2 | 5/2017 | Schaller et al. | |
| 9,668,641 B2 | 6/2017 | Ostrovsky et al. | |
| 9,763,678 B2 | 9/2017 | O'Neil et al. | |
| 2006/0058801 A1 | 3/2006 | Schlienger et al. | |
| 2008/0234691 A1 | 9/2008 | Schwab | |
| 2008/0294163 A1 | 11/2008 | Chou et al. | |
| 2009/0012565 A1 | 1/2009 | Sachs et al. | |
| 2009/0112262 A1 | 4/2009 | Pool et al. | |
| 2009/0118771 A1 | 5/2009 | Gonzlez-Hernandez | |
| 2009/0216232 A1 | 8/2009 | Buford, II et al. | |
| 2009/0228007 A1 | 9/2009 | Justin et al. | |
| 2009/0228008 A1 | 9/2009 | Justin et al. | |
| 2010/0331842 A1 | 12/2010 | Milbank | |
| 2011/0144703 A1 | 6/2011 | Krause et al. | |
| 2013/0103091 A1 | 4/2013 | Acosta, Jr. et al. | |
| 2013/0325021 A1 | 12/2013 | Beyar et al. | |
| 2015/0257800 A1 | 9/2015 | Harshman et al. | |
| 2018/0353214 A1 | 12/2018 | Kiester | |
| 2019/0328424 A1 | 10/2019 | Suddaby | |

FOREIGN PATENT DOCUMENTS

| | | |
|---|---|---|
| WO | WO2016/166663 | 10/2016 |
| WO | WO2017/201437 | 11/2017 |

OTHER PUBLICATIONS

Brochure. "ZIP Product Line, MIS Interspinous Fusion Systems", Surgical Technique Guide, Aurora Spine, Carlsbad, California, aurora-spine.com, 2014.

Mueller, Christian W. et al. "A Novel Shape Memory Plate Osteosynthesis for Noninvasive Modulation of Fixation Stiffness in a Rabbit Tibia Osteotomy Model", Hindawi Publishing Corporation, BioMed Research International, vol. 2015, Article ID 652940, 8 Pages, Http://dx.doi.org.

Barbosa, Lorena Monterio Cavalcanti et al. "Thermal Simulation of Electrical Heating of Shape Memory Alloys Wires Into A Polymeric Matrix With Two Different Sequences of Activation", 21st Brazilian Congress of Mechanical Engineering, Oct. 24-28, 2011, Natl, RN, Brazil.

Ali, Mohamed et al. "Selective RF wireless control of integrated bulk-micromachined shape-memory-alloy actuators and it's microfluidic application", Universiti Teknologi Malaysia Institutional Repository, Proceedings of the IEEE International Conference on Micro Electro Mechanical Systems (MEMS). IEEE, Cancun, http://eprints.utm.my/ID/eprint/29590., 2011, pp. 1269-1272.

\* cited by examiner

SEGMENTED ALIGNMENT ROD ASSEMBLY

CROSS-REFERENCE TO RELATED APPLICATIONS

This application is filed under 35 U.S.C. § 120 as a continuation-in-part of U.S. patent application Ser. No. 15/962,145, filed on Apr. 25, 2018, which application is hereby incorporated by reference in its entirety.

FIELD

The present disclosure relates to spinal alignment, and more particularly to a segmented alignment rod assembly for performing a gradual three-dimensional alignment of a spine which has deviated from a normal attitude for pathologic reasons.

BACKGROUND

Scoliosis is a disorder that causes an abnormal curve of the spine, or backbone. Patients with scoliosis develop abnormal curves to either side of the body's median line (lateral curve) and the bones of the spine twist on each other like a corkscrew.

The Greek physician Hippocrates coined the term scoliosis and devised various forms of external braces and benches to support or stretch the abnormally curved spine. Since animals can also suffer from scoliosis, there is little doubt it is an anomaly that has been around since the dawn of vertebrates. It is estimated that about 3% of humans are afflicted, meaning over 200 million people worldwide are living with this anomaly.

Females are much more likely to suffer from scoliosis than males and for idiopathic scoliosis the ratio is 10:1. It can be seen at any age, but it is most common in those over ten years old. Present knowledge suggests a genetically predisposed growth asymmetry at the level of the vertebral body endplates as a potential underlying cause.

Minor degrees of scoliosis are treated with bracing or stretching of the spine, not that dissimilar to the prescriptions and descriptions dating back to the time of Hippocrates. While the materials and techniques have changed, the principals have evolved very little.

Severe degrees of scoliosis are largely treated by a major operation known as segmental instrumented spinal fusion, a lengthy procedure where the muscles are flayed from the spinal bone and metal rods are then implanted to straighten the spine and hold it in position until grafted bone products fuse the spinal vertebrae together into a solid tower of bone. Since the normal spine is segmented to permit functional motion, fusion in and of itself sets the stage for life long corollary problems directly related to the administered cure which precludes normal movement, and at times, even normal growth.

Because of the magnitude of the surgery, complications include death, paralysis, infection, and hardware failure. Late complications include stiffness, chronic back pain, late hardware failure, and breakdown of adjacent normal segments because of stress provided by the long fused spinal segment. This list of complications is illustrative and not exhaustive.

Since major scoliosis surgery is such a cataclysmic event, it is often employed as a last resort, meaning that simple curves are followed until major curves develop thereby increasing not only the magnitude of the surgery, but the potential risk of complications as well.

Present scoliosis treatment is rather eclectic, employing everything from techniques of bracing, essentially outlined in the time of Hippocrates, to the major robotic surgeries of present day. As with anything in medicine, whenever multiple solutions exist for a particular disease process, it generally means that no single solution is sufficiently effective.

FIG. 1 is a stylized posterior view of a person P with a spine afflicted with scoliosis. Spinal column 1 is shown to have two lateral curves—upper curve 2 and lower curve 3. Often the presence of one lateral curve generates the formation of a second curve to compensate for the reduced spinal support of the body caused by one lateral curve. FIGS. 2 and 3 depict two different types of prior art braces 4 and 5, respectively, used to prevent further deterioration of spinal alignment. In some cases, braces such as braces 4 and 5 may improve the condition, but they rarely enable the wearer to achieve a full recovery to a correct spinal alignment.

Clearly, there is a need in the art to have a treatment that is simple and safe enough to employ such that spinal curvatures can be treated early in the pathologic process so that progression to major curvature can be avoided along with the attendant major interventional surgery required when the curves are extreme.

There is also a need in the art to diminish or eradicate the requirement for fusing the spine such that normal motion can be maintained, and the deleterious consequence of a spinal fusion avoided.

SUMMARY

According to aspects illustrated herein, there is provided a segmented rod assembly for aligning a spine including a plurality of vertebrae, comprising a rod, including a plurality of segments, the plurality of segments having at least a first segment arranged to be connected to a first vertebra of the spine, the first segment including a first body and at least one tang extending from the first body, and a second segment arranged to be connected to a second vertebra of the spine, the second segment including a second body and at least one channel arranged in the second body, wherein the at least one tang is operatively arranged to engage the at least one channel, and at least one tensioning member arranged within the plurality of segments, the at least one tensioning member having a first end secured to the first segment and a second end.

According to aspects illustrated herein, there is provided a segmented rod assembly for aligning a spine including a plurality of vertebrae, comprising a rod, including a plurality of segments, the plurality of segments having at least a first segment arranged to be connected to a first vertebra of the spine, a second segment arranged to be connected to a second vertebra of the spine, and a third segment arranged to be connected to a third vertebra of the spine, a first tensioning member arranged at least partially within the first segment and the second segment, and a second tensioning member arranged at least partially within the second segment and the third segment.

According to aspects illustrated herein, there is provided a segmented rod assembly for aligning a spine including a plurality of vertebrae, comprising a rod, including a plurality of segments, wherein a first segment of the plurality of segments includes a protruding tang, a second segment of the plurality of segments includes an outward facing channel, the protruding tang is operatively arranged to engage the outward facing channel to rigidly connect the first and second segments, and at least one segment of the plurality of segments is connected to a first vertebra of the spine, and at least one tensioning member arranged at least partially within the plurality of segments, wherein the at least one tensioning member is operatively arranged to force the plurality of segments into engagement.

According to aspects illustrated herein, there is provided a segmented rod assembly for aligning a spine having a plurality of vertebrae, comprising a rod, including a plurality of segments, the plurality of segments having at least a first segment arranged to be slidingly secured to a first vertebra of the spine, a second segment arranged to be fixedly secured to a second vertebra of the spine, and a third segment arranged between the first and second segments to be connected to a third vertebra of the spine, a tensioning member arranged within the plurality of segments, the tensioning member having a first end secured to the first segment and a second end.

According to aspect illustrated herein, there is provided a segmented rod assembly for aligning a spine having a plurality of vertebrae, comprising a first clamp arranged to be secured to a first vertebra of the spine, a second clamp arranged to be secured to a second vertebra of the spine, a third clamp arranged to be secured to a third vertebra of the spine, the third vertebra located between the first vertebra and the second vertebra, a rod, including a plurality of segments, the plurality of segments having at least a first segment slidingly engaged with the first clamp a second segment fixedly secured to the second clamp, and a third segment connected to the third clamp, and a line arranged within the plurality of segments, the line having a first end secured to the first segment and a second end, and a winding mechanism arranged proximate the second segment and connected to the second end.

A segmented rod assembly for aligning a spine having a plurality of vertebrae, comprising a first clamp arranged to be secured to a first vertebra of the spine, a second clamp arranged to be secured to a second vertebra of the spine, a third clamp arranged to be secured to a third vertebra of the spine, the third vertebra located between the first vertebra and the second vertebra, a rod, including a plurality of segments, the plurality of segments having at least a first segment slidingly engaged with the first clamp, a second segment fixedly secured to the second clamp, and a third segment connected to the third clamp, and a flexible shaft arranged within the plurality of segments, the flexible shaft having a first end secured to the first segment and a second end connected to the second segment, wherein when the flexible shaft is rotated in a first circumferential direction the plurality of segments are drawn toward each other to engage.

The present disclosure broadly comprises an assembly for performing a gradual three-dimensional alignment of a spine which has deviated from a normal attitude for pathologic reasons. The assembly includes a hollow segmented rod, having segments which, when drawn together, form a contoured rod whose reconfigured shape approximates an ideal or non-pathologic spinal configuration. A cable, or cables, is housed within the hollow segments that comprise the rod. In an example embodiment, a flexible shaft assembly is housed within the hollow segments that comprise the rod. The cable, cables, and flexible shaft is designed to draw the hollow segments together such that when the segments are intimately mated, they form a rigid rod that approximates an ideal spinal alignment. The cables or flexible shaft can be drawn taut by a turnbuckle at either or both ends. The cable or turnbuckle/flexible shaft assembly, in turn, are connected to a ratcheting worm drive assembly operated by a mechanically depressible subcutaneous paddle such that gradual spinal alignment can occur as the turnbuckle shortens the intersegmental distance between rod segments and rigid rod alignment is reestablished.

The present disclosure broadly comprises an assembly for performing gradual lateral alignment of a spine, gradual sagittal alignment of a spine, or a combination of the two, as well as correcting the rotation that invariably accompanies these deviations in severe combinations of the above malalignments. In essence, correction of three-dimensional malalignment.

The assembly comprises a hollow rod which is pre-contoured to approximate the normal S-shaped configuration of the human spine. The length of the rod and the approximate curves needed to correct the pathologic alignment of a patient is obtained using Surgimap® simulation software or similar software that provides computerized renderings of individual patient pathologies known in the art and presently utilized to form custom contoured patient-specific spinal rods for scoliosis surgery. Alternatively, a mathematical average for a specific spine length can be chosen and a statistical ideal curvature for the spine selected.

Once the ideal patient-specific rod is formed, it is cut into segments, with each segment being roughly the length of a vertebral body segment. In sections where little curvature is anticipated, a rod segment may span two or more vertebral segments. The preformed hollow rod is cut into segments such that each segment can deviate from the other in regard to their original axial alignment, when separated, but bond intimately in a male/female fashion when drawn together by a cable(s) or flexible shaft.

In an alternative embodiment, the adjacent segments are hinged together at a specific point at or near the circumference of the perimeter of the rod, such that the original curvilinear shape of the rod is approximated once the segments are drawn tautly together by an integrated connecting cable.

The hollow rod, once segmented, can be passed along the external surface of the spine and assume any of a myriad of pathologic configurations. The segmented rod is then affixed to the spine at the proximal and distal ends, and at the apex of the curvature, should complex rotatory curves be encountered. Individual segments are maintained in close juxtaposition by an interconnecting cable, which permits limited polyaxial movement of the segments. These segments are like beads on a string, render the construct flexible, but stiffen the construct when the string is drawn taut and the beads are pulled into close apposition. By varying the shape of the contact surfaces between the bead elements, different longitudinal shapes can be formed when the string is tautened.

The fixation of the rod to the spine will be through traditional methods known in the art such as hooks, clamps, screw, or combinations thereof. The preferred embodiment utilized a spinous process clamp which clamps two or more adjacent spinous processes. In an example embodiment, the spinous process clamp clamps only one spinous process. In the case of pedicle screws and the like, expansion screws are preferred and will be described infra.

Once the segmented rod is drawn subfacially along the pathologic spine and its curves, ideally along the spinous process/lamina junction, and affixed to the spine at two or more strategic locations, the segments are gradually drawn together to assume their original pre-segmented attitude, including the built-in contours necessary to restore perfect spinal alignment. By tensioning the cable over time, gradual spinal alignment can be achieved thereby mitigating traction injury to the spinal cord.

Drawing the segments of the rod together is accomplished in one of two ways. In highly flexible spines where forces are less likely to be extreme, the hinge and cable iteration would be chosen because it would utilize a thinner rod approximating a 5-6 mm diameter. Hinging of the segments would occur along the ventral portion of the rod where sagittal curve correction would be required and laterally where lateral curve correction is anticipated. While a round rod could be used, the hinged version may utilize an oval, or square cross-sectional shape to allow a greater surface area to employ a hinge linkage. In this version, the tautening cable would be located along the perimeter opposite the hinge, insofar as possible, to maximize the mechanical advantage. In stiffer spines, a larger 8-10 mm diameter segmented rod with a single large internal cable capable of withstanding greater force could be employed.

Once the cable rod is positioned along the spine, the hinged connection allows intimate contact of a particular rod segment with a corresponding vertebral element. The cranial and caudal segments are intimately secured via clamp, hook, or pedicle screw fixation, while the apex segment may be fixated via clamp, hook, pedicle screw, or also a cable to allow better relative movement between the alignment assembly and the spine while restoration of the spine to a normal attitude occurs. The rod segment assembly would be enclosed in a flexible sheath of biocompatible material to prevent tissue ingress or growth between rod segments, e.g., polyethylene.

Tautening of the cables occurs in the caudal segment, which houses a turnbuckle attached to the cable. A subcutaneous ratcheting worm drive mechanism is implanted in, on, or adjacent to the caudal segment and connected to a turnbuckle assembly such that when a subcutaneous paddle is digitally compressed transcutaneously through intact skin, the turnbuckle draws the cable taut thereby pulling the segments together and restoring ideal rod configuration. Since the spine is affixed to the rod, spinal movement mirrors rod movement until rigid configuration of the rod is restored. While one rod should be sufficient to restore alignment, a second rod could be employed to provide greater support of the scoliotic spine during straightening. Certain segments could connect in a ball and socket configuration to allow for limited movement of the spine thereby permitting some normal movement.

In another embodiment, a cable is replaced with a flexible rotary shaft capable of imparting both tensile and rotary forces. This shaft lies in roughly the center of the segments of the rod and is connected to a turnbuckle located at each end. Initially, the caudal turnbuckle is rotated, tensioning the system, and once it reaches maximal tensioning, it begins to rotate the flexible shaft which turns a second turnbuckle located at the cranial end. By employing two turnbuckles, even greater cable shortening and rod tensioning can occur.

To implant the segmented contoured cable rod assembly for gradual spinal alignment, the anesthetized patient is positioned prone on the operating table. After appropriate prepping and draping, fluoroscopy is used to identify the spinal curve apex as well as the cranial and caudal transition to normality. Each position is marked and a small incision is made to expose two spinous processes at each of the three indicated levels. To these exposed spinous processes, a special clamp is affixed serving to attach the segmented cable assembly to the spine. To pass the segmented cable rod assembly from one clamp to the other in subfacial location, a catheter passer is employed. Once the catheter passer is slid subfacially from one incision to another, a cable is slid through the hollow plastic sheath when the malleable trochar is removed. The wire is placed from one incision to the next entering the caudal incision, passing through the apex incision and emanating from the cranial incision. Alternatively, the cable can be passed from the cranial incision to the caudal incision, if desired. The catheter passer is removed leaving the cable behind.

Once the cable is positioned subfacially in a preferred location, the segmented cable rod assembly is attached to one end of the cable and pulled beneath the fascia along the contours of the spinal curvature. The cable rod assembly is then affixed to the spinous process clamps located at the cranial, caudal, and apex incisions.

In the preferred embodiment, the segmented cable rod assembly is securely affixed to the caudal clamp so that no relative motion, apart from segment apposition, can occur. To the caudal end of the caudal clamp, a ratcheting turnbuckle assembly is affixed and is used to draw the cable taut when a subcutaneous paddle is depressed.

In the apex incision, the segmented cable rod is affixed to the clamp such that it can slide relative to the clamp in an axial or longitudinal plane, but is restricted circumferentially by a collar. As the segmented cable rod assembly gradually straightens, it brings the spinous process clamp and spine along with it toward its new attitude. Since the rod can slide unrestricted, and has a sloppy fit, unrestricted spinal growth can occur along with some limited spinal movement. These features buffer the extremes of forces that cause failure in present day fixed scoliosis instrumented constructs, and permits a modicum of normal spinal movement for the child that rigid bracing or fusion deny.

At the superior end, the final segment of the cable rod construct affixes to the cranial clamp via a distal protuberance that engages the clamp in a piston/rod configuration. This association, similar to the collar fixation at the apex, allows for limited lateral/medial and dorsal/ventral movement while permitting linear axial movement as the child grows or whenever the child bends. The length of this slideable component is 5-7 cm to permit normal spinal growth elongation without having to lengthen the rod.

Once the assembly is affixed to the spine via the clamps the incisions are closed and allowed to heal.

Gradual spinal alignment is carried out by depressing a subcutaneous paddle beneath the skin at the level of the caudal clamp. This paddle activates a ratcheting worm drive turnbuckle assembly which tautens the cable, thereby drawing the segments of the rod closer together. As the segments approximate gradually, relative motion is restricted until a solid contoured rod assembly is formed, whereupon tightening is ceased. The rigid rod then serves to maintain normal contoured spinal alignment until mature spinal growth has been achieved. At this point, the cable is loosened and the patient is observed to ensure the mature spine does not lapse into misalignment. If it does not, the device assembly is removed, leaving a normal functioning spine. If deviation does occur, the cable assembly is retightened and fusion of the apex is carried out.

It is clear that the ratcheting worm drive mechanical activator of the present disclosure could be replaced with a magnetic, ultrasonic, or piezoelectric motor if desired. The manually operated activator is preferred in this invention so as to decrease the costs associated with this form of instrumented surgery.

Should pedicle screws be required or desired as a means of anchoring the assembly to the spine, a pedicle screw with an expansile shaft is preferred. The shaft is expanded once the screw is placed to increase surface area and mitigate "toggling" or "windshield wipering" of the shaft in softer cancellous bone when axial or perpendicular forces are applied to the shaft.

In some embodiments, the present disclosure uses motors (e.g., servo motors) similar to those used in robotics. For example, motors can be placed at various strategic locations along the segmented rod assembly to tighten various sections of the rod at different times. The motors may be triggered by slackness in its respective tensioning member or cable. Thus, a sensor detecting slackness in a tensioning member would trigger the motor connected thereto to activate and tighten the tensioning member. The motor may turn a threaded screw connected to the tensioning member to tighten the section of the rod.

In some embodiments, a servo motor may be arranged in each segment (i.e., every two segments is connected by a tensioning member). In some embodiments, the segmented rod assembly is separated into strategic sections according to the normal S-curve of a spine (e.g., based on vertebral height, the extent of the curvature of the deviated portion of the pathologic spine, etc.) and servo motors are assigned to each of those sections. Thus, tensioning members are arranged in series, rather than one long cable biased at the end of the segmented rod, which allows for better control of the corrective spinal alignment process. Springs could also be used instead of or in addition to the motors to bias the tensioning members of the segmented rod assembly.

The motors may be activated/controlled by sensing slackness in the tensioning members or may be controlled wirelessly via a wireless control and transducers. In some embodiments, muscle wire or bio metal is used for the tensioning members in order to tighten the sections of the segmented rod assembly.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be appreciated that the apex vertebra, apex, or apex of the curve is the vertebra or disk with the greatest rotation or farthest deviation from the center of the vertebral column. End vertebrae are those with the maximal tilt toward the apex of the curve.

Figure 1:
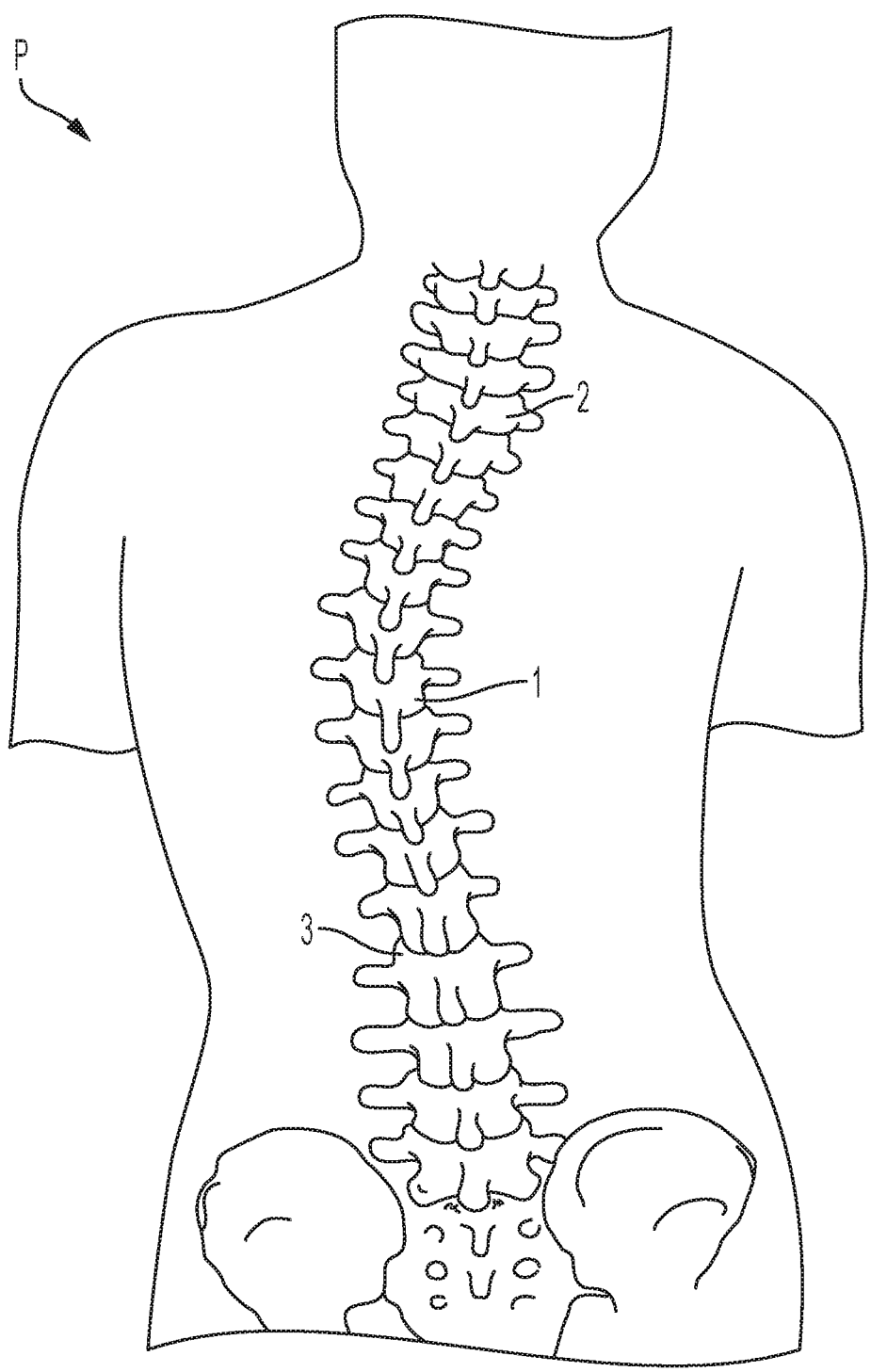
FIG. 1 is a stylized posterior view of a person with a spine afflicted with scoliosis.
Figure 2:
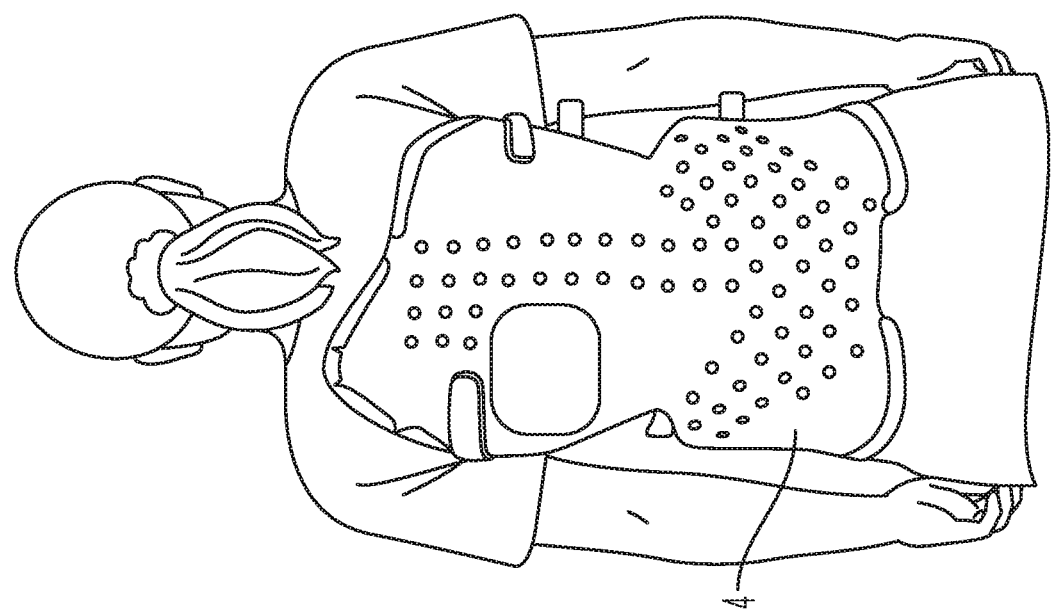
FIG. 2 is a rear view of a person with scoliosis wearing a full body brace as known in the prior art.
Figure 3:
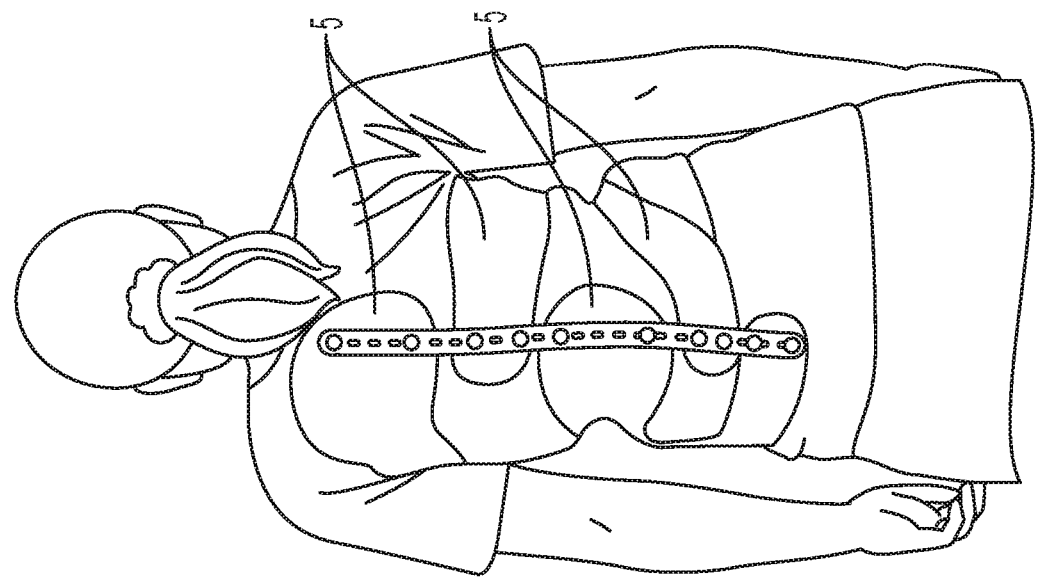
FIG. 3 is a rear view similar to that of FIG. 2 but showing a lighter prior art brace.
Figure 4A:
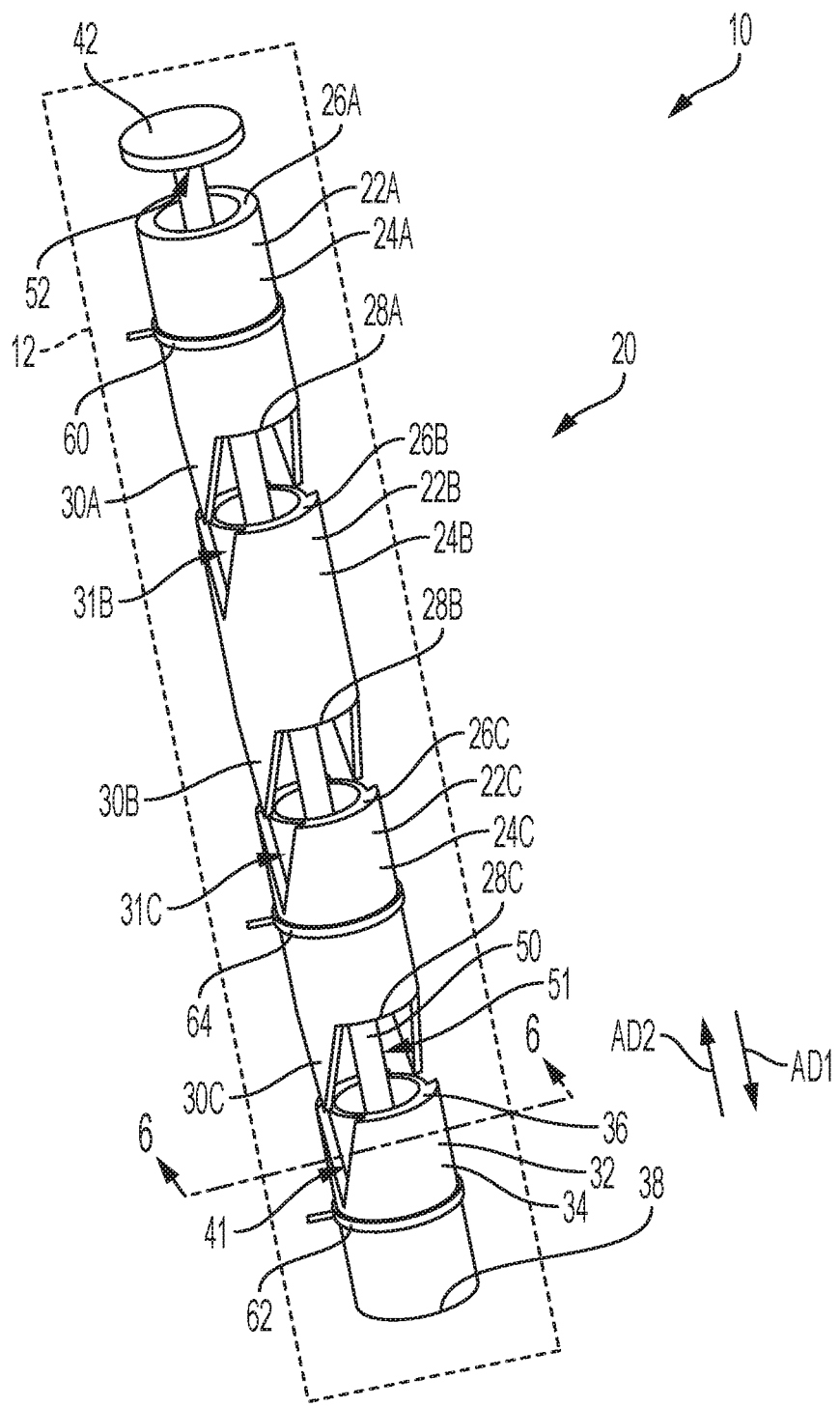
FIG. 4A is a perspective view of a segmented rod assembly.

Referring now to the figures, FIG. 4A is a perspective view of segmented rod assembly 10. Segmented rod assembly 10 comprises rod 20, tensioning member 50, and biasing element 200. Segmented rod assembly 10 may be enclosed or at least partially enclosed in a flexible sheath 12. In some embodiments, sheath 12 comprises a biocompatible material or fabric (e.g., polyethylene) to prevent tissue ingress or growth between rod segments.

Rod 20 comprises a plurality of segments arranged adjacent each other along tensioning member 50. In the embodiment shown, rod 20 is generally a hollow rod comprising segments 22A-C and 32. Segments 22A-C and 32 are substantially similar, but may differ slightly from each other and in length. Preferably, each of segments 22A-C and 32 comprises a length which is similar to that of the height of a vertebra. In an example embodiment, the segments arranged proximate an extreme curvature of a pathologic spine may comprise a smaller height than the segments proximate a straighter spine curvature. This arrangement allows for a more gradual and efficient straightening of the pathologic spine. Rod 20 may comprise plastic (e.g., polyethylene), titanium, chromium, cobalt, or any other suitable material.

Segment 22A comprises body 24A, end 26A, end 28A, and one or more tangs 30A. Tangs 30A are connected to end 28A and extend therefrom. Tangs 30A are arranged to engage channels 31B of segment 22B. In some embodiments, tangs 30A are arranged in alignment with an outer surface of body 24A (i.e., the radially outward facing surface of tangs 30A are aligned with the radial outward facing surface of body 24A). In some embodiments, and as shown, tangs 30A are generally triangular shaped and form a point or rounded point. The triangular shape of tangs 30A allow segment 22A to laterally pivot/flex, and rotate, with respect to segment 22B. It should be appreciated, however, that tangs 30A may comprise any geometry suitable for gradually engaging an adjacent segment, for example, rectangular, circular, semi-circular, ovular, trapezoidal, etc. Segment 22A further comprises a through-bore that extends from end 26A to end 28A, thereby allowing tensioning member 50 to pass at least partially therethrough. By arranging tangs 30A on or proximate the outer surface of body 24A, a more substantial (i.e., thicker) tensioning member 50 may be used as there is no tapered portion of segment 22A arranged to engage the through-bore of segment 22B.

Segment 22B comprises body 24B, end 26B, end 28B, one or more tangs 30B, and one or more channels 31B. Tangs 30B are connected to end 28B and extend therefrom. Tangs 30B are arranged to engage channels 31C of segment 22C. In some embodiments, tangs 30B are arranged in alignment with an outer surface of body 24B (i.e., the radially outward facing surface of tangs 30B are aligned with the radial outward facing surface of body 24B). In some embodiments, and as shown, tangs 30B are generally triangular shaped and form a point or rounded point. The triangular shape of tangs 30B allows segment 22B to laterally pivot/flex, and rotate, with respect to segment 22C. It should be appreciated, however, that tangs 30B may comprise any geometry suitable for gradually engaging an adjacent segment, for example, rectangular, circular, semi-circular, ovular, trapezoidal, etc. Segment 22B further comprises a through-bore that extends from end 26B to end 28B, thereby allowing tensioning member 50 to pass at least partially therethrough. By arranging tangs 30B on or proximate the outer surface of body 24B, a more substantial (i.e., thicker) tensioning member 50 may be used as there is no tapered portion of segment 22B arranged to engage the through-bore of segment 22C. Channels 31B are generally notches/indentations in the outer surface of body 24B arranged proximate end 26B. In some embodiments, and as shown, channels 31B are triangular shaped such that they are engageable with tangs 30A of segment 22A. As previously discussed, the engagement of the generally triangular-shaped tangs 30A with channels 31B allows segment 22A to pivot/flex and rotate with respect to segment 22B when tangs 30A are partially engaged with channels 31B. When tangs 30A are fully engaged with channels 31B and force is applied appropriately by tensioning member 50, segment 22A is rigidly secured to segment 22B, as will be described in greater detail below.

Segment 22C comprises body 24C, end 26C, end 28C, one or more tangs 30C, and one or more channels 31C. Tangs 30C are connected to end 28C and extend therefrom. Tangs 30C are arranged to engage channels 41 of segment 32. In some embodiments, tangs 30C are arranged in alignment with an outer surface of body 24C (i.e., the radially outward facing surface of tangs 30C are aligned with the radial outward facing surface of body 24C). In some embodiments, and as shown, tangs 30C are generally triangular shaped and form a point or rounded point. The triangular shape of tangs 30C allows segment 22C to laterally pivot/flex, and rotate, with respect to segment 32. It should be appreciated, however, that tangs 30C may comprise any geometry suitable for gradually engaging an adjacent segment, for example, rectangular, circular, semi-circular, ovular, trapezoidal, etc. Segment 22C further comprises a through-bore that extends from end 26C to end 28C, thereby allowing tensioning member 50 to pass at least partially therethrough. By arranging tangs 30C on or proximate the outer surface of body 24C, a more substantial (i.e., thicker) tensioning member 50 may be used as there is no tapered portion of segment 22C arranged to engage the through-bore of segment 32. Channels 31C are generally notches/indentations in the outer surface of body 24C arranged proximate end 26C. In some embodiments, and as shown, channels 31C are triangular shaped such that they are engageable with tangs 30B of segment 22B. As previously discussed, the engagement of the generally triangular-shaped tangs 30B with channels 31C allows segment 22B to pivot/flex and rotate with respect to segment 22C when tangs 30B are partially engaged with channels 31C. When tangs 30B are fully engaged with channels 31C and force is applied appropriately by tensioning member 50, segment 22B is rigidly secured to segment 22C, as will be described in greater detail below.

Segment 32 comprises body 34, end 36, end 38, and one or more channels 41. Segment 32 further comprises a through-bore that extends from end 36 to end 38, thereby allowing tensioning member 50 to pass at least partially therethrough. Channels 41 are generally notches/indentations in the outer surface of body 34 arranged proximate end 36. In some embodiments, and as shown, channels 41 are triangular shaped such that they are engageable with tangs 30C of segment 22C. As previously discussed, the engagement of the generally triangular-shaped tangs 30C with channels 41 allows segment 22C to pivot/flex and rotate with respect to segment 32 when tangs 30C are partially engaged with channels 41. When tangs 30C are fully engaged with channels 41 and force is applied appropriately by tensioning member 50, segment 22C is rigidly secured to segment 32, as will be described in greater detail below. Biasing element 200 may be arranged within or proximate to segment 32, as will be discussed in greater detail below.

It should be appreciated that rod 20 may comprise any number of segments (e.g., a plurality of segments) suitable to be secured to and gradually straighten a pathologic spine, and that this disclosure is not limited to only the use of four segments. As is apparent to one having ordinary skill in the art, rod 20 must comprise enough segments to adequately canvas the subject curvature of the pathologic spine. Further, it should be appreciated that while the segments of rod 20 are shown to be generally cylindrical (i.e., the cross-sectional geometry of each section is circular), the segments may comprise any suitable cross-sectional geometry (e.g., square, rectangular, ovular, ellipsoidal, trapezoidal, polygonal, etc.).

Tensioning member 50 is arranged inside of rod 20. Specifically, tensioning member 50 passes at least partially through segments 22A-C and 32. In the embodiment shown, tensioning member 50 is embodied as line 51 having end 52 and end 54. Line 51 may be a cable, plurality of cables, string, rope, chain, or any other flexible material suitable to draw segments 22A-C and 32 together upon tautening. End 52 is connected to plate 42. Plate 42 is arranged to abut against or connect to end 26A. In some embodiments, plate 42 is integrally formed with segment 22A and is fixed to end 26A. In some embodiments, end 52 is connected to segment 22A. End 54 is connected to a tensioning or biasing element (e.g., biasing element 200). The arrangement of segments 22A-C and 32 on line 51 resembles that of beads on a string. As line 51 is tautened via biasing element 200, plate 42 pulls segments 22A-C and 32 together. As segments 22A-C and 32 begin to engage, rod 20 becomes increasingly rigid. Once segments 22A-C and 32 are fully engaged, rod 20 resembles a single rigid rod (see FIG. 4B).

In some embodiments, end 54 may be connected to a turnbuckle rod which threadably engages segment 32. Specifically, the turnbuckle rod is a threaded rod which threadably engages end 38 at a first end and has a hook at its second end which is connected to end 54 of line 51. As the turnbuckle rod is rotated, the hook pulls end 54 toward end 38 and thereby tautens line 51. In some embodiments, end 52 may be connected to a turnbuckle rod which threadably engages segment 22A. Specifically, the turnbuckle rod is a threaded rod which threadably engages end 26A at a first end and has a hook at its second end which is connected to end 52 of line 51. As the turnbuckle rod is rotated, the hook pulls end 52 toward end 26A and thereby tautens line 51. In an example embodiment, there are turnbuckles arranged in both segment 22A and 32. Line 51 may be connected to a hook on the respective turnbuckle rod via a loop or directly connected to the respective turnbuckle via welding, adhesives, etc.

Segmented rod assembly 10 further comprises a plurality of anchors. As shown, segmented rod assembly 10 comprises anchors 60, 62, and 64 for connecting rod 20 to the pathologic spine. Anchor 60 is slidably connected to segment 22A and is secured to a cranial vertebra using, for example, a spinous process clamp, a pedicle screw, or other similar method of fixation. Anchor 60 is slidably connected to segment 22A such that as the pathologic spine straightens, and thereby lengthens, segmented rod assembly 10 adjusts to the length of the spine. To account for the increase in length, segment 22A may be significantly longer than the other segments. Anchor 62 is fixedly secured to segment 32 and is secured to a caudal vertebra using, for example, a spinous process clamp, a pedicle screw, or other similar method of fixation. In some embodiments, anchor 62 is slidably secured to segment 32. Anchor 64 is slidably connected to segment 22C and is connected to the apex vertebra. Similar to anchor 60, anchor 64 is slidably connected to segment 22C to adjust for the straightening and lengthening of the spine. In an example embodiment, anchor 64 is fixedly connected to segment 22C. It should be appreciated that anchor 64 does not need to be slidably connected to segment 22C, but can be connected to any segment that is arranged near the apex vertebra such that the pathologic spine may be suitably straightened.

Figure 4B:
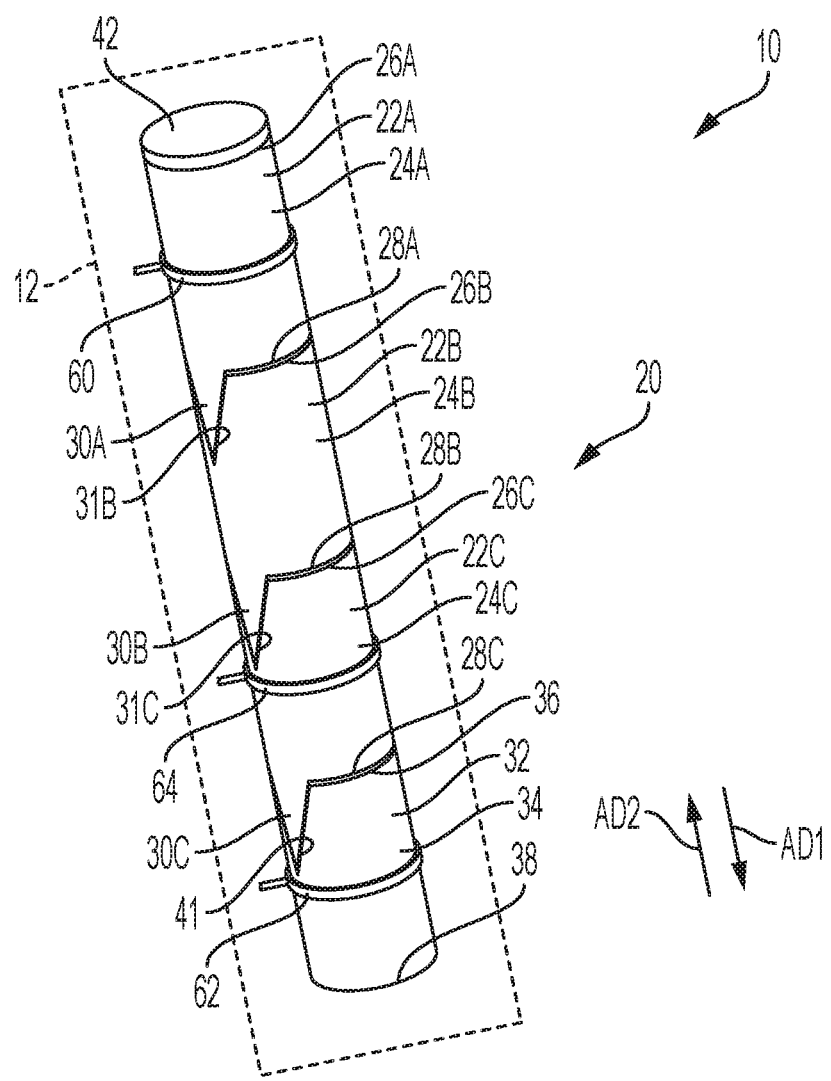
FIG. 4B is a perspective view of the segmented rod assembly shown in FIG. 4A, in a rigid rod alignment.

FIG. 4B is a perspective view of segmented rod assembly 10 in a rigid rod alignment. As shown, the segments of rod 20 are fully engaged with each other. Line 51 is tautened by biasing element 200 such that plate 42 is pulled toward biasing element 200 (i.e., generally in axial direction AD1). Plate 42 abuts against end 26A of segment 22A. Tangs 30A are fully engaged with channels 31B of segment 22B such that end 28A abuts against end 26B. Tangs 30B are fully engaged with channels 31C of segment 22C such that end 28B abuts against end 26C. Tangs 30C are fully engaged with channels 41 of segment 32 such that end 28C abuts against end 36. It should be appreciated that even when the tangs are fully engaged with the channels, there may still be flexion within rod 20 to allow for normal flexion of a spine.

It should be appreciated that rod 20, when rigid, does not need to form a linear rod. The design of rod 20, when rigid, imitates the normal curvature of the human spine (i.e., thoracic curvature, sacral curvature, lumbar curvature, cervical curvature, lateral curvature, etc.). FIG. 4B demonstrates simply how the various segments engage in order form a rigid rod. The rod shown in FIG. 4B could be employed to correct lateral curvature of a pathologic spine.

Figure 5:
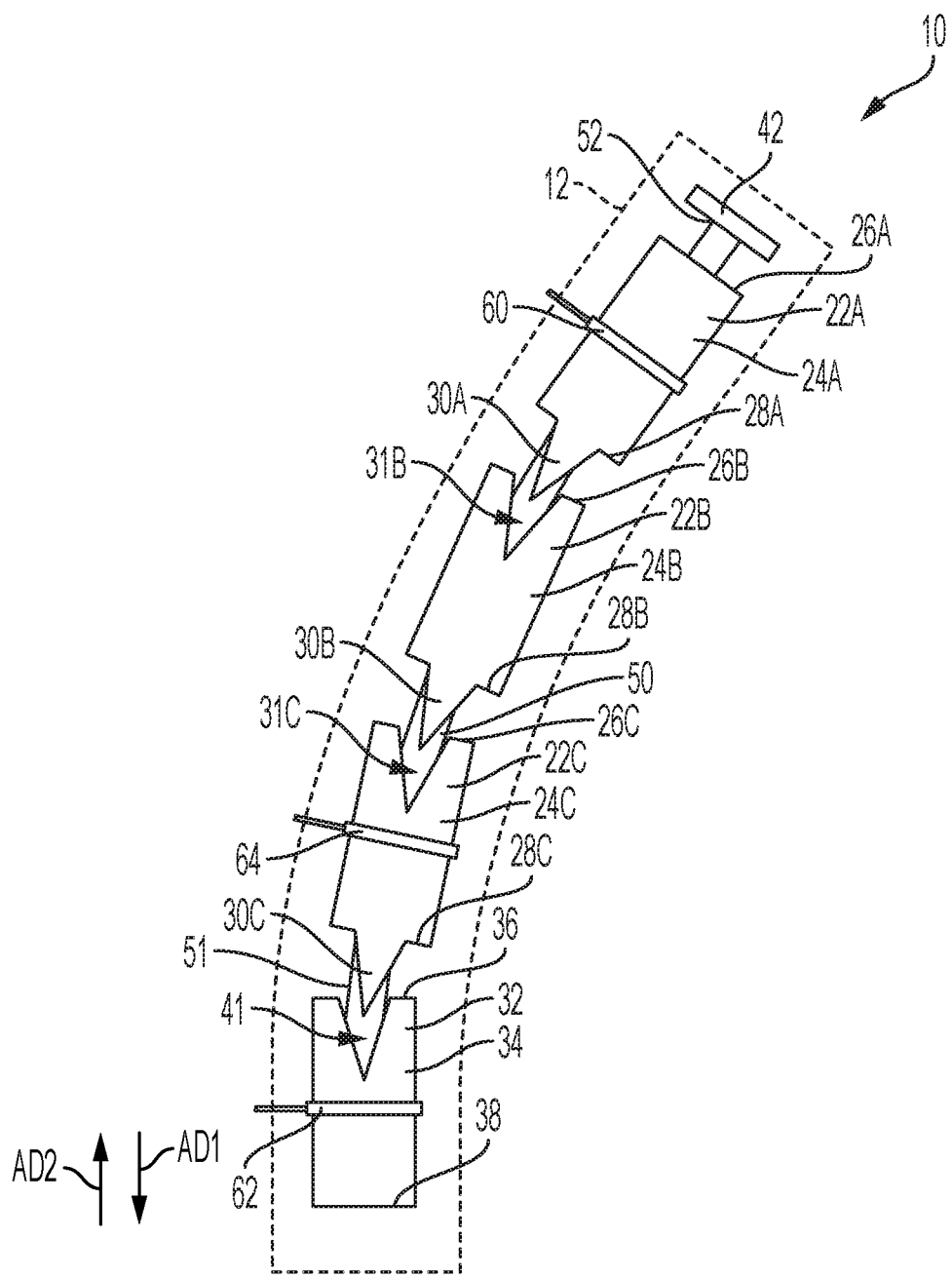
FIG. 5 is a side elevational view of the segmented rod assembly shown in FIG. 4A.

FIG. 5 is a side elevational view of segmented rod assembly 10. In the most disengaged state (i.e., when the tangs are barely engaged with the channels of an adjacent segment), the segments are capable of the most movement with respect to each other (i.e., segments may pivot, flex, and rotate with respect to each other). As tensioning member 50 is drawn in axial direction AD1 and the tangs further engage the channels, less movement between the segments occurs. Thus, the more engaged the tangs are with the channels, the stiffer rod 20 becomes.

Figure 6:
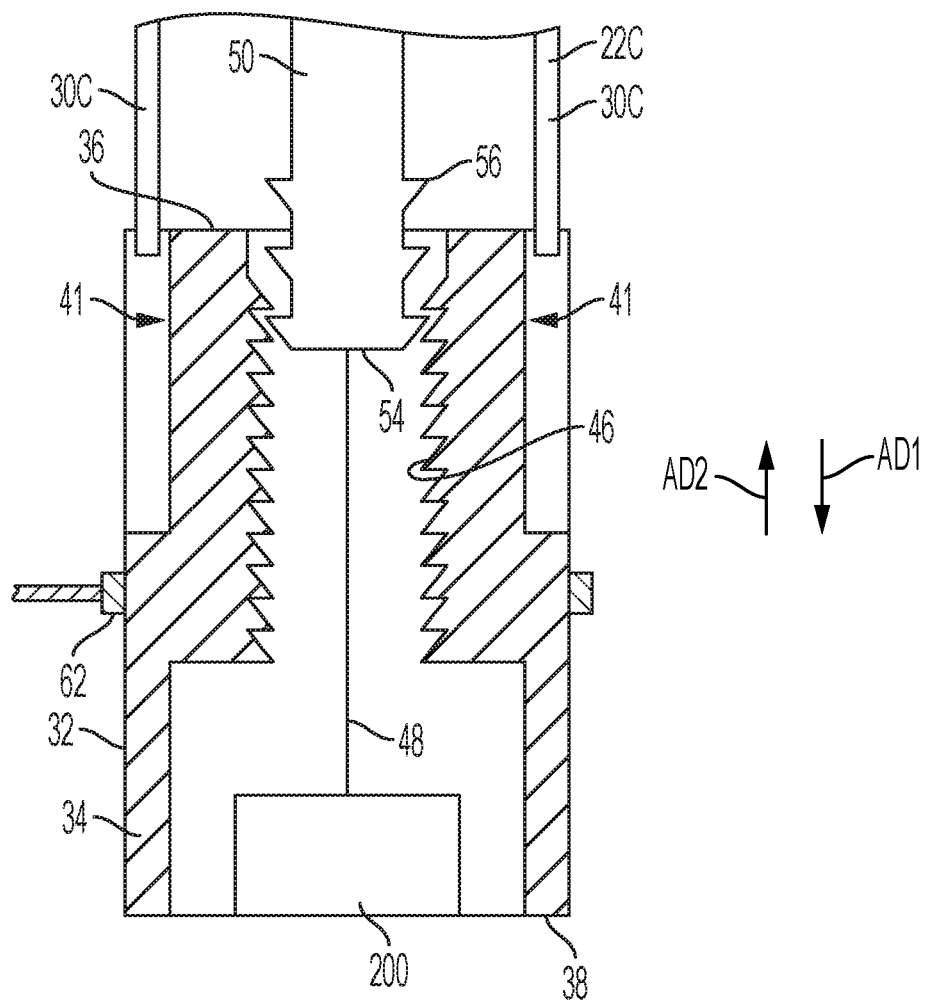
FIG. 6 is a partial cross-sectional view of the segmented rod assembly taken generally along line 6-6 in FIG. 4A.

FIG. 6 is a partial cross-sectional view of segmented rod assembly 10 taken generally along line 6-6 in FIG. 4A. Specifically, FIG. 6 shows a cross-sectional view of segment 32. In some embodiments, and as shown, biasing element 200 is arranged in segment 32 in order to bias tensioning member 50 generally in axial direction AD1. In some embodiments, biasing element 200 comprises a motor, for example, a direct current (DC) motor (e.g., a coreless brushed DC motor, a servo motor, etc.). The motor of biasing element 200 may be used instead of or in addition to a spring biasing mechanism. In some embodiments, the motor of biasing element 200 may be triggered by slackness sensed in tensioning member 50, and thus segmented rod assembly 10 may comprise one or more sensors operatively arranged to detect slack in tensioning member 50 and communicate with biasing element 200. In such embodiments, the slackness in tensioning member 50 would trigger a sensor that starts the motor and the motor would turn and wind tensioning member 50. In some embodiments, the motor turns a threaded screw connected to tensioning member 50 to tauten tensioning member 50. In some embodiments, the motor of biasing element 200 may be activated wirelessly, via a wireless controller. It should be appreciated that biasing element 200 may be alternatively arranged adjacent or proximate to end 38, outside of segment 32.

In some embodiments, tensioning member 50 comprises one or more muscle wires. As is known in the art, muscle wires or bio metal are easily stretched by a small force. However, when an electrical current is introduced therein, the wire heats and changes to a much harder form that returns to the unstretched shape, and thus the wire shortens with a usable amount of force. In some embodiments, tensioning member 50 comprises one or more muscle wires and biasing element 200 is operatively arranged to introduce an electric current into tensioning member 50, such that tensioning member 50 shortens and biases segment 22A toward segment 32. Electric current may be introduced into tensioning member 50 via a servo based receiving unit.

Further, in some embodiments, and as shown, segment 32 may comprise one or more teeth 46 operatively arranged to engage one or more teeth 56 arranged on tensioning member 50. The engagement of teeth 56 with 46 allows tensioning member 50 to displace in axial direction AD1 but not axial direction AD2. In some embodiments, segment 32 comprises a ratchet assembly that engages with teeth 56 that allows tensioning member 50 to displace in axial direction AD1 but not axial direction AD2. Biasing element 200 may be directly connected to tensioning member 50 or may be connected through connector 48. In some embodiments biasing element 200 comprises a worm drive and/or a ratchet assembly.

Figure 7:
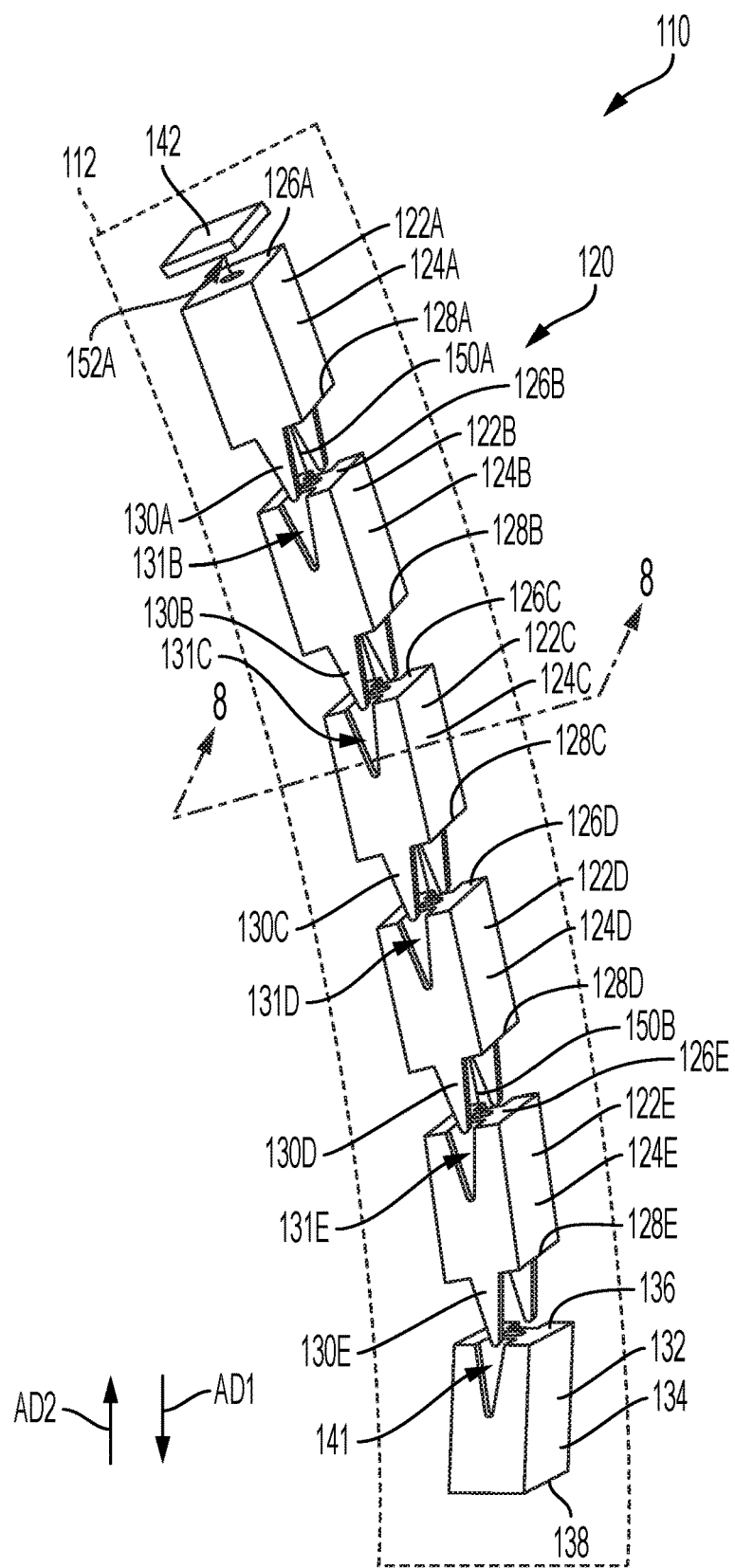
FIG. 7 is a perspective view of a segmented rod assembly.
Figure 8:
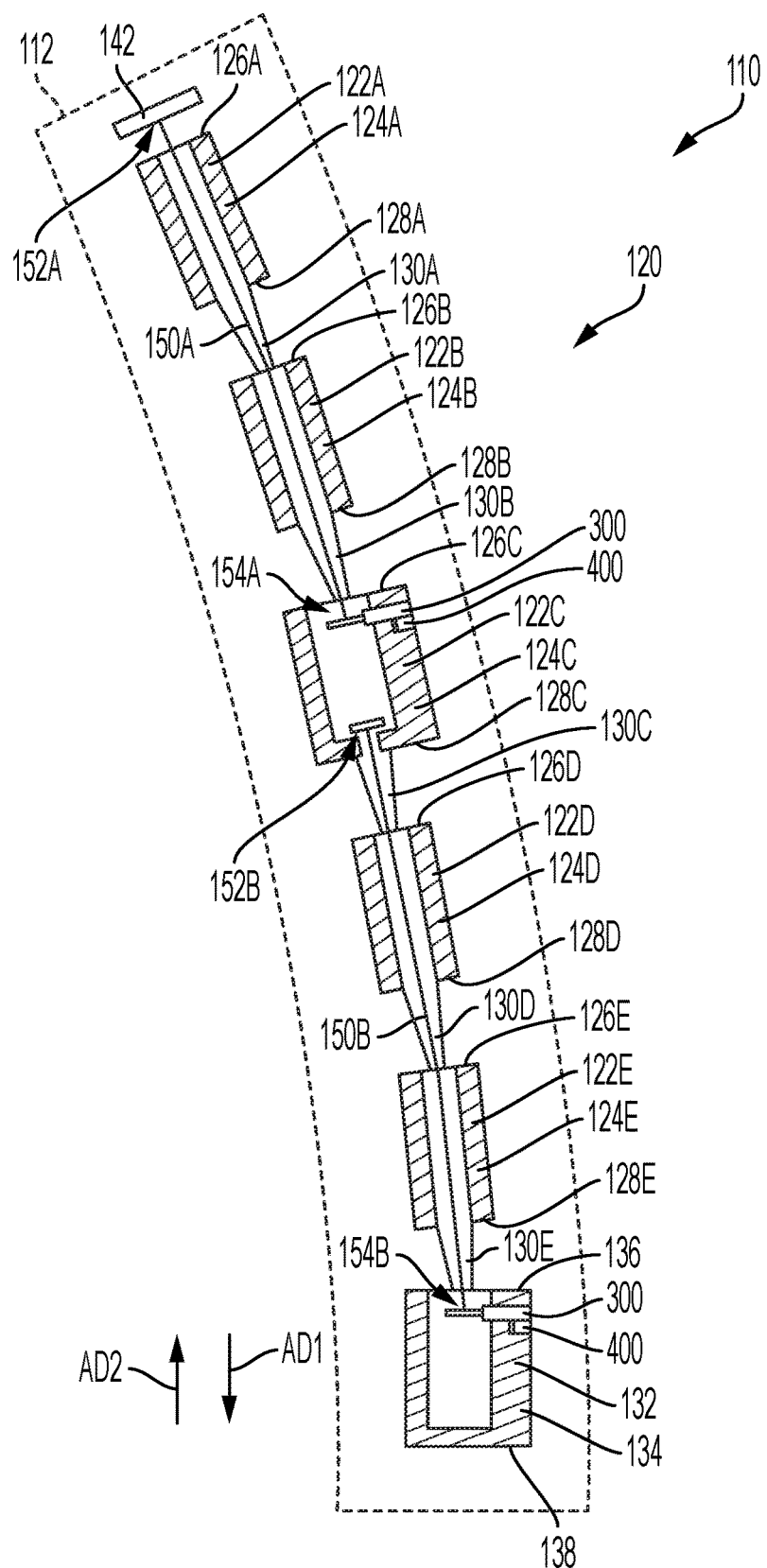
FIG. 8 is a cross-sectional view of the segmented rod assembly taken generally along line 8-8 in FIG. 7.

FIG. 7 is a perspective view of segmented rod assembly 110. FIG. 8 is a cross-sectional view of segmented rod assembly 110 taken generally along line 8-8 in FIG. 7.

Segmented rod assembly 110 comprises rod 210, at least one tensioning member (e.g., tensioning members 150A-B), and one or more biasing elements 300. Segmented rod assembly 110 may be enclosed or at least partially enclosed in a flexible sheath 112. In some embodiments, sheath 112 comprises a biocompatible material or fabric (e.g., polyethylene) to prevent tissue ingress or growth between rod segments.

Rod 120 comprises a plurality of segments arranged adjacent each other along tensioning members 150A-B. In the embodiment shown, rod 120 is generally a hollow rod comprising segments 122A-E and 132. Segments 122A-E and 132 are substantially similar, but may differ slightly from each other and in length. Preferably, each of segments 122A-E and 132 comprises a length which is similar to that of the height of a vertebra. In an example embodiment, the segments arranged proximate an extreme curvature of a pathologic spine may comprise a smaller height than the segments proximate a straighter spine curvature. This arrangement allows for a more gradual and efficient straightening of the pathologic spine. Rod 120 may comprise plastic (e.g., polyethylene), titanium, chromium, cobalt, or any other suitable material.

Segment 122A comprises body 124A, end 126A, end 128A, and one or more tangs 130A. Tangs 130A are connected to end 128A and extend therefrom. Tangs 130A are arranged to engage channels 131B of segment 122B. In some embodiments, tangs 130A are arranged in alignment with an outer surface of body 124A (i.e., the radially outward facing surface of tangs 130A are aligned with the radial outward facing surface of body 124A). In some embodiments, and as shown, tangs 130A are generally triangular shaped and form a point or rounded point. The triangular shape of tangs 130A allow segment 122A to laterally pivot/flex, and rotate, with respect to segment 122B. It should be appreciated, however, that tangs 130A may comprise any geometry suitable for gradually engaging an adjacent segment, for example, rectangular, circular, semi-circular, ovular, trapezoidal, etc. Segment 122A further comprises a through-bore that extends from end 126A to end 128A, thereby allowing tensioning member 150A to pass at least partially therethrough. By arranging tangs 130A on or proximate the outer surface of body 124A, a more substantial (i.e., thicker) tensioning member 150A may be used as there is no tapered portion of segment 122A arranged to engage the through-bore of segment 122B.

Segment 122B comprises body 124B, end 126B, end 128B, one or more tangs 130B, and one or more channels 131B. Tangs 130B are connected to end 128B and extend therefrom. Tangs 130B are arranged to engage channels 131C of segment 122C. In some embodiments, tangs 130B are arranged in alignment with an outer surface of body 124B (i.e., the radially outward facing surface of tangs 130B are aligned with the radial outward facing surface of body 124B). In some embodiments, and as shown, tangs 130B are generally triangular shaped and form a point or rounded point. The triangular shape of tangs 130B allows segment 122B to laterally pivot/flex, and rotate, with respect to segment 122C. It should be appreciated, however, that tangs 130B may comprise any geometry suitable for gradually engaging an adjacent segment, for example, rectangular, circular, semi-circular, ovular, trapezoidal, etc. Segment 122B further comprises a through-bore that extends from end 126B to end 128B, thereby allowing tensioning member 150A to pass at least partially therethrough. By arranging tangs 130B on or proximate the outer surface of body 124B, a more substantial (i.e., thicker) tensioning member 150A may be used as there is no tapered portion of segment 122B arranged to engage the through-bore of segment 122C. Channels 131B are generally notches/indentations in the outer surface of body 124B arranged proximate end 126B. In some embodiments, and as shown, channels 131B are triangular shaped such that they are engageable with tangs 130A of segment 122A. As previously discussed, the engagement of the generally triangular-shaped tangs 130A with channels 131B allows segment 122A to pivot/flex and rotate with respect to segment 122B when tangs 130A are partially engaged with channels 131B. When tangs 130A are fully engaged with channels 131B and force is applied appropriately by tensioning member 150A, segment 122A is rigidly secured to segment 122B, as will be described in greater detail below.

Segment 122C comprises body 124C, end 126C, end 128C, one or more tangs 130C, and one or more channels 131C. Tangs 130C are connected to end 128C and extend therefrom. Tangs 130C are arranged to engage channels 131D of segment 122D. In some embodiments, tangs 130C are arranged in alignment with an outer surface of body 124C (i.e., the radially outward facing surface of tangs 130C are aligned with the radial outward facing surface of body 124C). In some embodiments, and as shown, tangs 130C are generally triangular shaped and form a point or rounded point. The triangular shape of tangs 130C allows segment 122C to laterally pivot/flex, and rotate, with respect to segment 122D. It should be appreciated, however, that tangs 130C may comprise any geometry suitable for gradually engaging an adjacent segment, for example, rectangular, circular, semi-circular, ovular, trapezoidal, etc. Segment 122C further comprises a through-bore that extends from end 126C to end 128C, thereby allowing tensioning members 150A-B to pass at least partially therethrough. By arranging tangs 130C on or proximate the outer surface of body 124C, more substantial (i.e., thicker) tensioning members 150A-B may be used as there is no tapered portion of segment 122C arranged to engage the through-bore of segment 122D. Channels 131C are generally notches/indentations in the outer surface of body 124C arranged proximate end 126C. In some embodiments, and as shown, channels 131C are triangular shaped such that they are engageable with tangs 130B of segment 122B. As previously discussed, the engagement of the generally triangular-shaped tangs 130B with channels 131C allows segment 122B to pivot/flex and rotate with respect to segment 122C when tangs 130B are partially engaged with channels 131C. When tangs 130B are fully engaged with channels 131C and force is applied appropriately by tensioning member 150A, segment 122B is rigidly secured to segment 122C, as will be described in greater detail below. Biasing element 300 may be arranged within or proximate to segment 122C, as will be discussed in greater detail below.

Segment 122D comprises body 124D, end 126D, end 128D, one or more tangs 130D, and one or more channels 131D. Tangs 130D are connected to end 128D and extend therefrom. Tangs 130D are arranged to engage channels 131E of segment 122E. In some embodiments, tangs 130D are arranged in alignment with an outer surface of body 124D (i.e., the radially outward facing surface of tangs 130D are aligned with the radial outward facing surface of body 124D). In some embodiments, and as shown, tangs 130D are generally triangular shaped and form a point or rounded point. The triangular shape of tangs 130D allows segment 122D to laterally pivot/flex, and rotate, with respect to segment 122E. It should be appreciated, however, that tangs 130D may comprise any geometry suitable for gradually engaging an adjacent segment, for example, rectangular, circular, semi-circular, ovular, trapezoidal, etc. Segment 122D further comprises a through-bore that extends from end 126D to end 128D, thereby allowing tensioning member 150B to pass at least partially therethrough. By arranging tangs 130D on or proximate the outer surface of body 124D, a more substantial (i.e., thicker) tensioning member 150B may be used as there is no tapered portion of segment 122D arranged to engage the through-bore of segment 122E. Channels 131D are generally notches/indentations in the outer surface of body 124D arranged proximate end 126D. In some embodiments, and as shown, channels 131D are triangular shaped such that they are engageable with tangs 130C of segment 122C. As previously discussed, the engagement of the generally triangular-shaped tangs 130C with channels 131D allows segment 122C to pivot/flex and rotate with respect to segment 122D when tangs 130C are partially engaged with channels 131D. When tangs 130C are fully engaged with channels 131D and force is applied appropriately by tensioning member 150B, segment 122C is rigidly secured to segment 122D, as will be described in greater detail below.

Segment 122E comprises body 124E, end 126E, end 128E, one or more tangs 130E, and one or more channels 131E. Tangs 130E are connected to end 128E and extend therefrom. Tangs 130E are arranged to engage channels 141 of segment 132. In some embodiments, tangs 130E are arranged in alignment with an outer surface of body 124E (i.e., the radially outward facing surface of tangs 130E are aligned with the radial outward facing surface of body 124E). In some embodiments, and as shown, tangs 130E are generally triangular shaped and form a point or rounded point. The triangular shape of tangs 130E allows segment 122E to laterally pivot/flex, and rotate, with respect to segment 132. It should be appreciated, however, that tangs 130E may comprise any geometry suitable for gradually engaging an adjacent segment, for example, rectangular, circular, semi-circular, ovular, trapezoidal, etc. Segment 122E further comprises a through-bore that extends from end 126E to end 128E, thereby allowing tensioning member 150 to pass at least partially therethrough. By arranging tangs 130E on or proximate the outer surface of body 124E, a more substantial (i.e., thicker) tensioning member 150B may be used as there is no tapered portion of segment 122E arranged to engage the through-bore of segment 132. Channels 131E are generally notches/indentations in the outer surface of body 124E arranged proximate end 126E. In some embodiments, and as shown, channels 131E are triangular shaped such that they are engageable with tangs 130D of segment 122D. As previously discussed, the engagement of the generally triangular-shaped tangs 130D with channels 131E allows segment 122D to pivot/flex and rotate with respect to segment 122E when tangs 130D are partially engaged with channels 131E. When tangs 130D are fully engaged with channels 131E and force is applied appropriately by tensioning member 150B, segment 122D is rigidly secured to segment 122E, as will be described in greater detail below.

Segment 132 comprises body 134, end 136, end 138, and one or more channels 141. Segment 132 further comprises a through-bore that extends from end 136 to end 138, thereby allowing tensioning member 150 to pass at least partially therethrough. Channels 141 are generally notches/indentations in the outer surface of body 134 arranged proximate end 136. In some embodiments, and as shown, channels 141 are triangular shaped such that they are engageable with tangs 130E of segment 122E. As previously discussed, the engagement of the generally triangular-shaped tangs 130E with channels 141 allows segment 122E to pivot/flex and rotate with respect to segment 132 when tangs 130E are partially engaged with channels 141. When tangs 130E are fully engaged with channels 141 and force is applied appropriately by tensioning member 150B, segment 122E is rigidly secured to segment 132, as will be described in greater detail below. Biasing element 300 may be arranged within or proximate to segment 132, as will be discussed in greater detail below.

It should be appreciated that rod 120 may comprise any number of segments (e.g., a plurality of segments) suitable to be secured to and gradually straighten a pathologic spine, and that this disclosure is not limited to only the use of six segments. As is apparent to one having ordinary skill in the art, rod 120 must comprise enough segments to adequately canvas the subject curvature of the pathologic spine. Further, it should be appreciated that while the segments of rod 120 are shown to be generally square/rectangular (i.e., the cross-sectional geometry of each section is square/rectangular), the segments may comprise any suitable cross-sectional geometry (e.g., circular, ovular, ellipsoidal, trapezoidal, polygonal, etc.).

Tensioning members 150A-B are arranged inside of rod 120. Specifically, tensioning member 150A passes at least partially through segments 122A-C and tensioning member 150B passes at least partially through segments 122C-E and 132. It should be appreciated that any number of tensioning members may be used (e.g., one or more tensioning members), and that each tensioning member may pass through any number of segments. For example, in some embodiments, a first tensioning member is arranged to connect segments 122A-B, a second tensioning member is arranged to connect segment 122B-C, a third tensioning member is arranged to connect segments 122C-E, and a fourth tensioning member is arranged connect segments 122E and 132. By using multiple tensioning members to connect various segments throughout rod 120, the force required to pull the segments into full engagement with each other is less than the force required with one tensioning member throughout all of the segments. In the embodiment shown, tensioning member 150A comprises end 152A and end 154A, and tensioning member 150B comprises end 152B and end 154B. Each of tensioning members 150A-B may comprise a cable, plurality of cables, string, rope, chain, or any other flexible material suitable to draw segments 122A-E and 132 together upon tautening. End 152A is connected to plate 142. Plate 142 is arranged to abut against or connect to end 126A. In some embodiments, plate 142 is integrally formed with segment 122A and is fixed to end 126A. In some embodiments, end 152A is connected to segment 122A. End 154A is connected to a tensioning or biasing element (e.g., biasing element 300) arranged in another segment (e.g., segment 122C). The arrangement of segments 122A-C on tensioning member 150A resembles that of beads on a string. As tensioning member 150A is tautened via biasing element 300, plate 142 pulls segments 122A-C together. As segments 122A-C begin to engage, rod 120 becomes increasingly rigid. Once segments 122A-C are fully engaged, that portion of rod 120 resembles a single rigid rod. End 152B is connected to segment 122C. End 154B is connected to a tensioning or biasing element (e.g., biasing element 300) arranged in another segment (e.g., segment 132). The arrangement of segments 122C-E and 132 on tensioning member 150B resembles that of beads on a string. As tensioning member 150B is tautened via biasing element 300, segments 122C-E and 132 together are pulled together. As segments 122C-E and 132 begin to engage, that portion of rod 120 becomes increasingly rigid. Once segments 122C-E and 132 are fully engaged, that portion of rod 120 resembles a single rigid rod.

Segmented rod assembly 110 may further comprises a plurality of anchors. For example, segmented rod assembly 100 may comprise three anchors to connect segmented rod assembly 110 to the pathologic spine, as previously discussed with respect to segmented rod assembly 10.

Similar to that of segmented rod assembly 10, the segments of rod 120 are fully engageable with each other (see FIGS. 9A-D). Tensioning members 150A-B are tautened by biasing elements 300 to pull segments 122A-E and 132 together. When fully engaged, plate 142 abuts against end 126A of segment 122A. Tangs 130A are fully engaged with channels 131B of segment 122B such that end 128A abuts against end 126B. Tangs 130B are fully engaged with channels 131C of segment 122C such that end 128B abuts against end 126C. Tangs 130C are fully engaged with channels 131D of segment 122D such that end 128C abuts against end 126D. Tangs 130D are fully engaged with channels 131E of segment 122E such that end 128D abuts against end 126E. Tangs 130E are fully engaged with channels 141 of segment 132 such that end 128E abuts against end 136. It should be appreciated that even when the tangs are fully engaged with the channels, there may still be flexion within rod 120 to allow for normal flexion of a spine.

It should be appreciated that rod 120, when rigid, does not need to form a linear rod. The design of rod 120, when rigid, imitates the normal curvature of the human spine (i.e., thoracic curvature, sacral curvature, lumbar curvature, cervical curvature, lateral curvature, etc.). FIGS. 9A-D demonstrate how the various segments engage in order form a rigid rod to correct lateral curvature of a pathologic spine, while maintaining the normal curvature of the spine.

In the most disengaged state (i.e., when the tangs are barely engaged with the channels of an adjacent segment), the segments are capable of the most movement with respect to each other (i.e., segments may pivot, flex, and rotate with respect to each other). As tensioning member 150A and/or 150B is taughtened and the tangs further engage the channels, less movement between the segments occurs. Thus, the more engaged the tangs are with the channels, the stiffer rod 120 becomes.

In some embodiments, one or more biasing elements 300 are arranged in or proximate to one or more segments throughout segmented rod assembly 110. For example, as shown in FIG. 8, biasing elements 300 are arranged in segments 122C and 132 in order to bias tensioning member 150A and 150B, respectively, generally in axial direction AD1. In some embodiments, each of biasing elements 300 comprises a motor, for example, a direct current (DC) motor (e.g., a coreless brushed DC motor, a servo motor, etc.). The motor of biasing element 300 may be used instead of or in addition to a spring biasing mechanism. In some embodiments, the motor of biasing element 300 may be triggered by slackness sensed in tensioning members 150A-B, and thus segmented rod assembly 110 may comprise one or more sensors operatively arranged to detect slack in tensioning members 150A-B and communicate with biasing element 300. In such embodiments, slackness in tensioning members 150A-B would trigger a sensor that starts the motor and the motor would turn and wind tensioning members 150A and/or 150B. In some embodiments, the motor turns a threaded screw connected to the respective tensioning member to tauten the tensioning member. In some embodiments, the motor of biasing element 300 may be activated wirelessly, via a wireless controller. For example, and as shown, each of biasing elements 300 may comprise a respective transducer 400. Transducer 400 is operatively arranged to receive a signal from a remote location, for example from controller 410 (see FIG. 9B), and activate or deactivate biasing element 300. In such embodiments, transducer 400 may receive a signal from control 410 and activate biasing element 300 to pull its respective tensioning member (e.g., 150A) thereby tightening its respective segments (e.g., segments 122A-C). Transducer 400 may also receive a signal from control 410 to deactivate biasing element 300 such that biasing element 300 discontinues pulling the respective tensioning member and instead maintains its functional length. It should be appreciated that biasing elements 300 may be alternatively arranged adjacent or proximate to the segments.

In some embodiments, tensioning member 150A and/or 150B comprises one or more muscle wires. As is known in the art, muscle wires or bio metal are easily stretched by a small force. However, when an electrical current is introduced therein, the wire heats and changes to a much harder form that returns to the unstretched shape, and thus the wire shortens with a usable amount of force. In some embodiments, tensioning member 150A and/or 150B comprises one or more muscle wires and biasing element 300 is operatively arranged to introduce an electric current into the respective tensioning member, such that the tensioning member shortens and biases the segments together.

Further, and as previously described, in some embodiments one or more segments of segmented rod assembly 110 may comprise teeth or a ratchet assembly in order to allow the tensioning members to be pulled in a first direction but not a second direction. For example, tensioning member 150A may comprise teeth proximate end 154A that engage teeth or a ratchet assembly in segment 122C that allows tensioning member 150A to displace generally in axial direction AD1 but not axial direction AD2. Similarly, tensioning member 150B may comprise teeth proximate end 154B that engage teeth or a ratchet assembly in segment 132 that allows tensioning member 150B to displace in axial direction AD1 but not axial direction AD2. In some embodiments biasing elements 300 comprise a worm drive and/or a ratchet assembly.

Figure 9A:
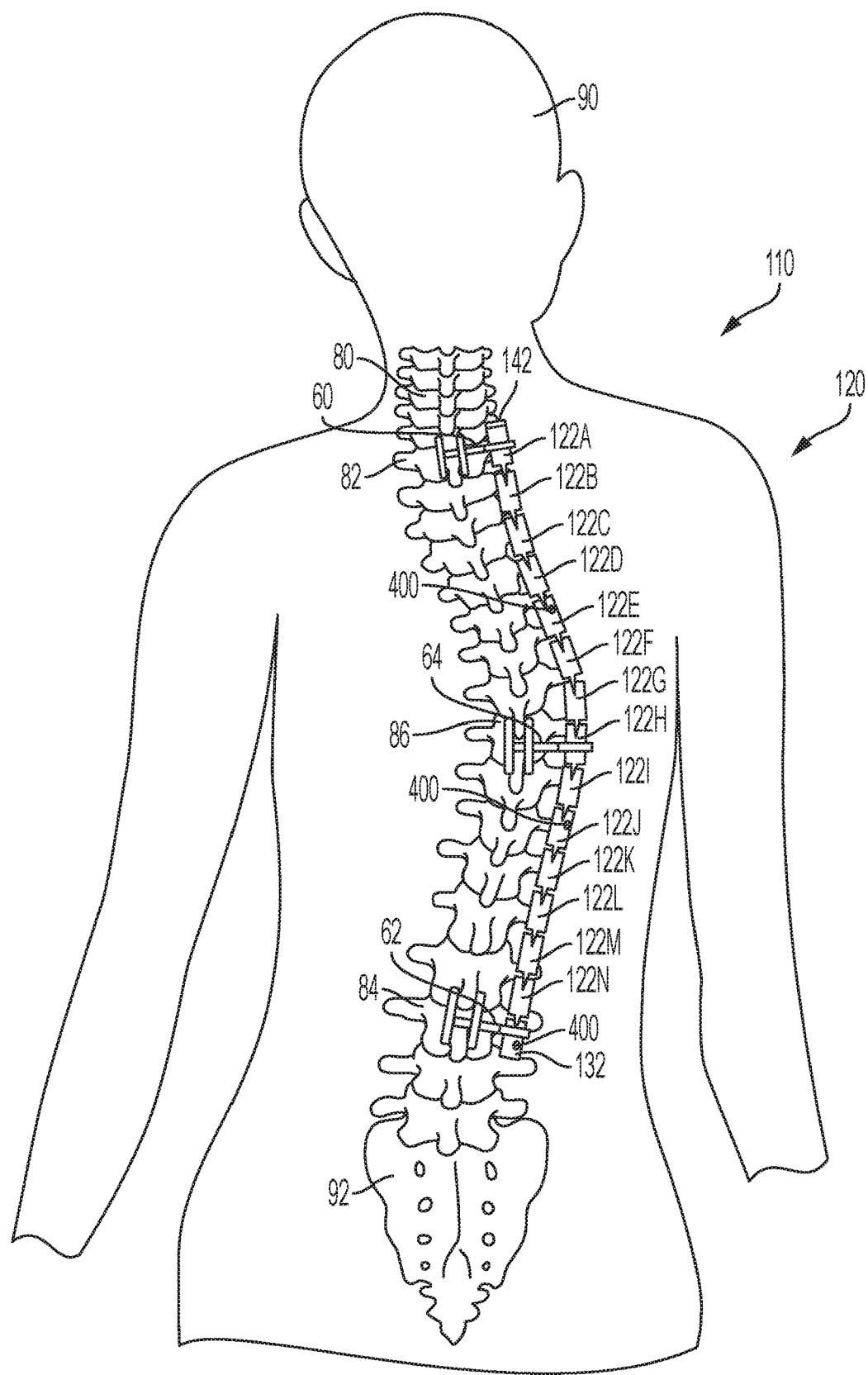
FIG. 9A is a posterior elevational view of a segmented rod assembly connected to a pathologic spine.

FIG. 9A is a posterior elevational view of segmented rod assembly 110 connected to (pathologic) spine 80. In the embodiment shown, rod 120 comprises segments 122A-N and 132 and three tensioning members (not shown). Segment 122A is slidably secured to cranial vertebra 82 via anchor 60. Cranial vertebra 82 is a vertebra of spine 80 generally located proximate cranium 90. Cranial vertebra 82 may also be the end vertebra of the curve on the cranial side. As is known in the art, the end vertebra of a curve is that with the maximal tilt toward the apex of the curve. Anchor 60 may be secured to the spinous process of cranial vertebra 82 using, for example, a spinous process clamp, pedicle screw, or any other suitable securing means. Segment 132 is fixedly secured to caudal vertebra 84 via anchor 62. In some embodiments, segment 132 is slidably connected to a caudal vertebra via anchor 62. Caudal vertebra 84 is a vertebra of spine 80 generally located proximate coccyx 92. Caudal vertebra 82 may also be the end vertebra of the curve on the caudal side. As is known in the art, the end vertebra of a curve is that with the maximal tilt toward the apex of the curve. Anchor 62 may be secured to the spinous process of caudal vertebra 84 using, for example, a spinous process clamp, pedicle screw, or any other suitable securing means. Segment 122H is connected to apex vertebra 86 via anchor 64. Apex vertebra 86 is a vertebra of spine 80 with the greatest rotation or farthest deviation from the center of the vertebral column. Anchor 64 may be secured to the spinous process of apex vertebra 86 using, for example, a spinous process clamp, pedicle screw, or any other suitable securing means. As shown, the tensioning members (not shown) have not yet been tautened, leaving segments 122B-N (and 132) to float relative to spine 80. Segment 122A may slide relative to spine 80. Segment 132 is fixedly secured to caudal vertebra 84 and therefore cannot move relative to spine 80. Segment 122H may be fixedly secured or slidingly connected to apex vertebra 86. Plate 142 is shown unconnected to segment 122A (as a separate component) however, in an example embodiment, plate 142 is fixedly secured to or integrally formed with segment 122A. It should be appreciated that segmented rod assembly 110 may be arranged on the opposite side of spine 80 (i.e., the left side). Segmented rod assembly 110 is shown offset from the vertebrae of spine 80. However, it should be appreciated that segmented rod assembly 110 can be arranged along the spino-laminar junction. It should also be appreciated that two segmented rod assemblies may be used on either side of the spinous process of spine 80 for added force.

Figure 9B:
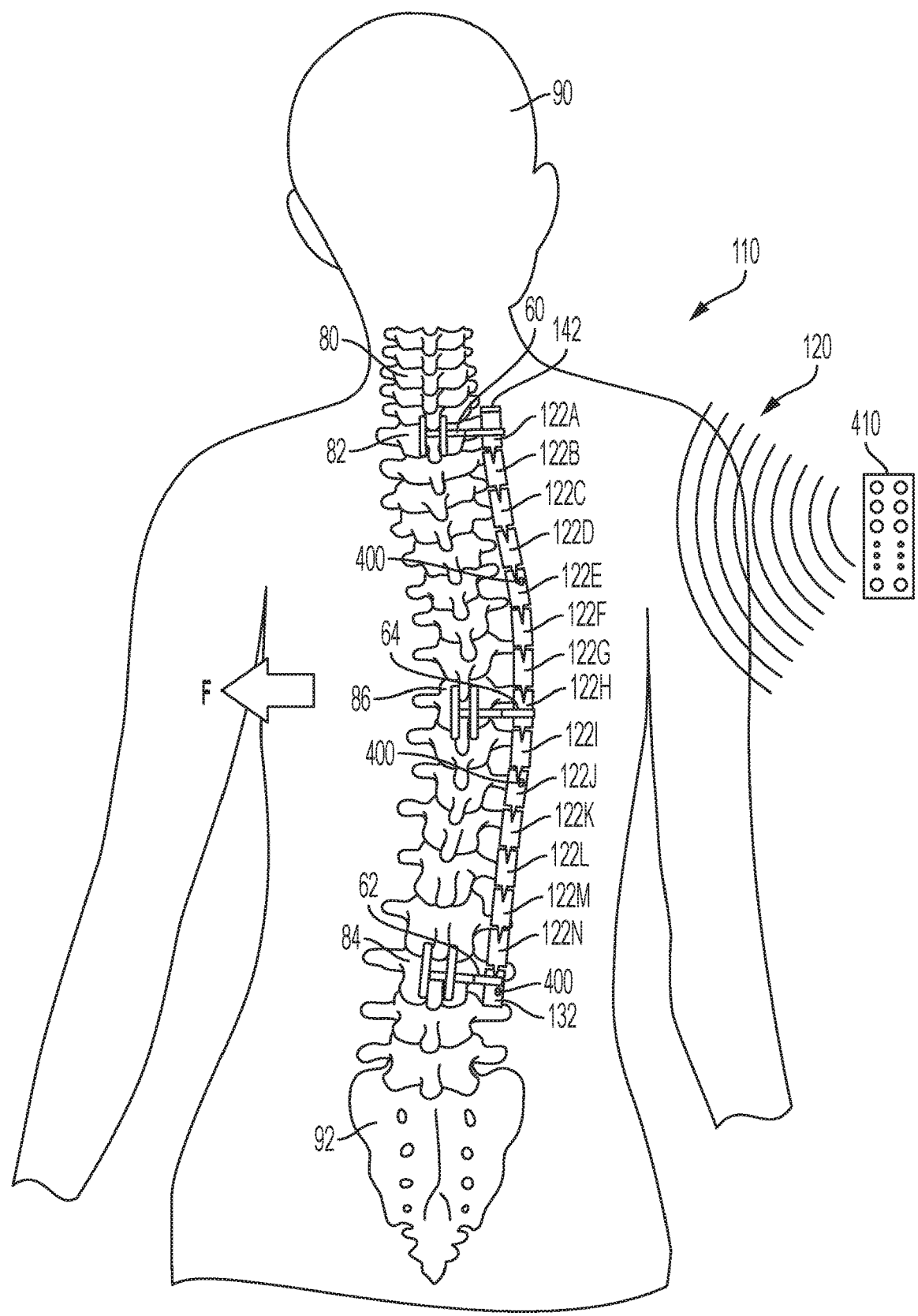
FIG. 9B is a posterior elevational view of the segmented rod assembly connected to the pathologic spine shown in FIG. 9A, with the segmented rod assembly partially engaged.

FIG. 9B is a posterior elevational view of segmented rod assembly 110 connected to (pathologic) spine 80. As shown, the tensioning members have been tautened via biasing elements 300 and segmented rod assembly 110 is partially engaged. Segments 122A-N and 132 of rod 120 are at least partially engaged with each other. Some of segments 122A-N and 132 may be fully engaged with each other. The tensioning members, for example, tensioning members 150A-C, should be taut, which results in straightening forces being asserted on (pathologic) spine 80. The straightening forces in the embodiment shown are designated by arrow F. Over time, these straightening forces will displace apex vertebra 86, and adjacent vertebrae, back into alignment with the rest of the vertebral column and thereby straighten spine 80. In the embodiment shown, segmented rod assembly 110 "pushes" apex vertebra 86 toward alignment with cranial vertebra 82 and caudal vertebra 84. However, segmented rod assembly 10 could be arranged on the opposite side of spine 80 (left side), and "pull" apex vertebra 86 toward alignment with cranial vertebra 82 and caudal vertebra 84.

In the embodiment shown, there are three tensioning members: a first tensioning member connecting plate 142 and segments 122A-E, a second tensioning member connecting segments 122E-122J, and a third tensioning member connecting segments 122J-N and 132. A biasing element 300 having transducer 400 is arranged in segment 122E and connected to the first tensioning member, a biasing element 300 having transducer 400 is arranged in segment 122J and connected to the second tensioning member, and a biasing element 300 having transducer 400 is arranged in segment 132 and connected to the third tensioning member. Each biasing element 300 is arranged to communicate with control 410 via its respective transducer. Thus, each of the three tensioning members, representing three sections of rod 120, may be taughtened independently of the other tensioning members. Also, the force required to pull rod 120 into full engagement is split amongst three biasing elements.

Figure 9C:
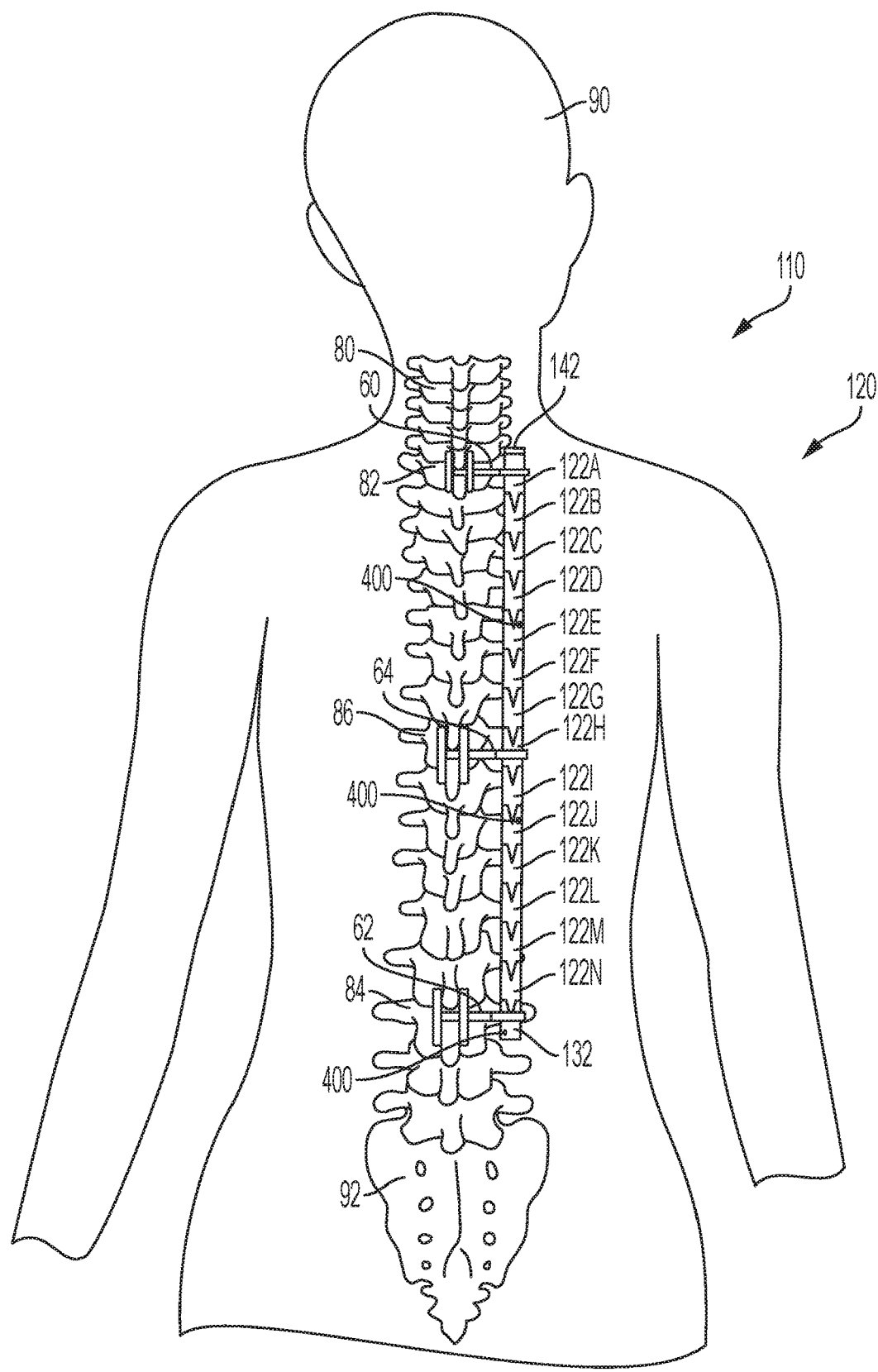
FIG. 9C is a posterior elevational view of the segmented rod assembly connected to the pathologic spine shown in FIG. 9A, with the segmented rod assembly fully engaged; and, FIG. 9D is a sagittal elevational view of the segmented rod assembly connected to the pathologic spine shown in FIG. 9C.
Figure 9D:
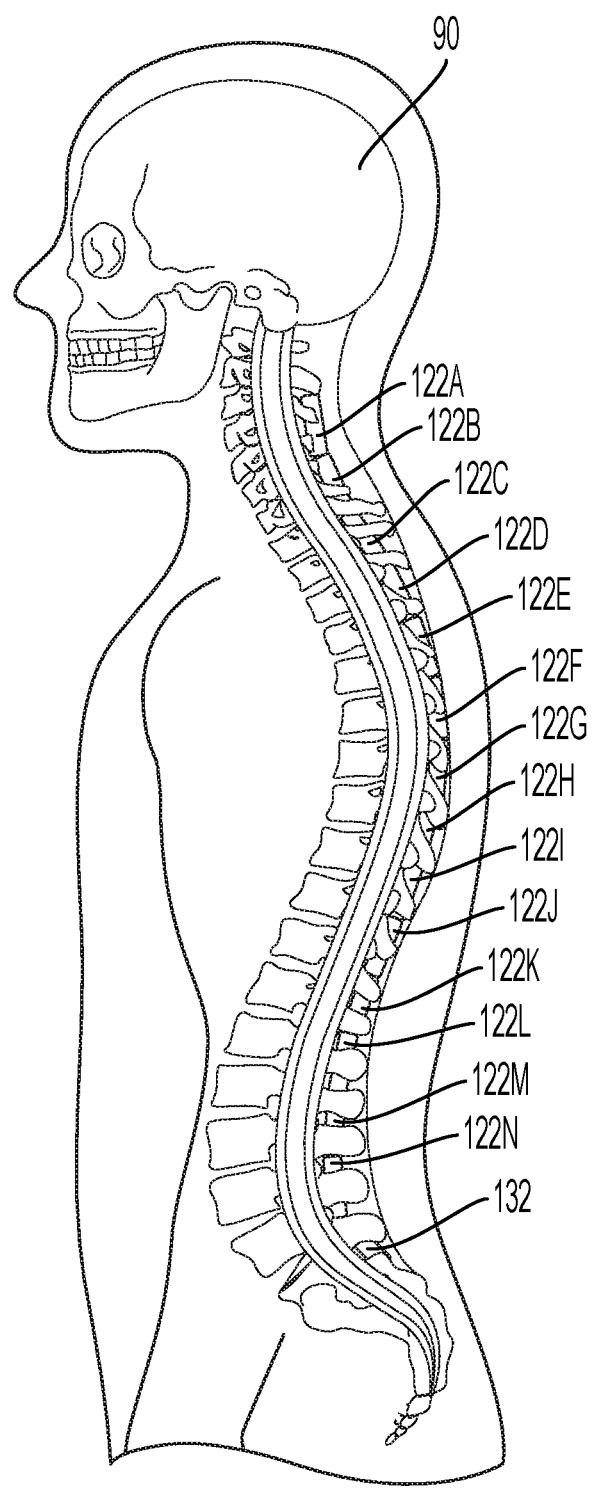

FIG. 9C is a posterior elevational view of segmented rod assembly 110 connected to spine 80 with rod 120 fully engaged. FIG. 9D is a sagittal elevational view of segmented rod assembly 110 connected to spine 80 with rod 120 fully engaged. As shown, the tensioning members have been further tautened via biasing elements 300 and segmented rod assembly 110 is fully engaged. Segments 122A-N and 132 of rod 120 (i.e., their respective tangs and channels), are fully engaged with each other, which allows rod 120 to take its final rigid shape. It should be appreciated that, although rigid rod 120 is shown to be linear, rigid rod 120 can be designed with three-dimensional curvature to best suit the patient (see FIG. 9D). As shown, apex vertebra 86 has been aligned with cranial vertebra 82 and caudal vertebra 84 to form a straightened spine 80.

It should be appreciated that the various segments of the present disclosure may be hollow or may be solid having a through-bore through which the tensioning member(s) extends. It should also be appreciated that the various segments of the present disclosure may include a plurality of through-bores through which a plurality of tensioning members extend.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

P Person
1 Spinal column
2 Upper curve
3 Lower curve
4 Brace
5 Brace
10 Segmented rod assembly
12 Sheath
20 Rod
22A Segment
22B Segment
22C Segment
24A Body
24B Body
24C Body
26A End
26B End
26C End
28A End
28B End
28C End
30A Tang(s)
30B Tang(s)
30C Tang(s)
31A Channel(s)
31B Channel(s)
31C Channel(s)
32 Segment
34 Body
36 End
38 End 41 Channel(s)
42 Plate
46 Teeth
48 Connector
50 Tensioning member
51 Line
52 End
54 End
56 Teeth
60 Anchor
62 Anchor
64 Anchor
80 Spine
82 Cranial vertebra
84 Caudal vertebra
86 Apex vertebra
90 Cranium
92 Coccyx
110 Segmented rod assembly
112 Sheath
120 Rod assembly
122A Segment
122B Segment
122C Segment
122D Segment
122E Segment
122F Segment
122G Segment
122H Segment
122I Segment
122J Segment
122K Segment
122L Segment
122M Segment
122N Segment
124A Body
124B Body
124C Body
124D Body
124E Body
126A End
126B End
126C End
126D End
126E End
128A End
128B End
128C End
128D End
128E End
130A Tang(s)
130B Tang(s)
130C Tang(s)
130D Tang(s)
130E Tang(s)
131B Channel(s)
131C Channel(s)
131D Channel(s)
131E Channel(s)
132 Segment
134 Body
136 End
138 End
141 Channel(s)
142 Plate
150A Tensioning member
150B Tensioning member
152A End
152B End
154A End
154B End
200 Biasing element
300 Biasing element
400 Transducer
410 Control
AD1 Axial direction
AD2 Axial direction
F Force

What is claimed is:

1. A segmented rod assembly for aligning a spine including a plurality of vertebrae, comprising:
a rod, including:
a plurality of segments, the plurality of segments comprising at least:
a first segment arranged to be connected to a first vertebra of the spine, the first segment including a first body and at least one tang extending from the first body; and,
a second segment arranged to be connected to a second vertebra of the spine, the second segment including a second body comprising a top end, a bottom end, an outer surface extending from the top end to the bottom end, and at least one channel arranged in the outer surface, wherein the at least tang is operatively arranged to engage the at least one channel; and,
at least one tensioning member arranged within the plurality of segments, the at least one tensioning member including a first end secured to the first segment and a second end.

2. The segmented rod assembly as recited in claim 1, further comprising a biasing element connected to the second end and operatively arranged to bias the at least one tensioning member in a first direction.

3. The segmented rod assembly as recited in claim 2, wherein the biasing element is arranged in the second segment.

4. The segmented rod assembly as recited in claim 3, wherein the biasing element comprises a servo motor.

5. The segmented rod assembly as recited in claim 3, wherein:
the tensioning member comprises a plurality of teeth;
the second segment comprises at least one element; and,
the at least one element is operatively arranged to engage the plurality of teeth to prevent displacement of the tensioning member in a second direction, opposite the first direction.

6. The segmented rod assembly as recited in claim 1, wherein each of the plurality of segments are operatively arranged to engage with an adjacent segment.

7. The segmented rod assembly as recited in claim 6, wherein the second segment further comprises a tang connected to the bottom end and the at least one channel is arranged proximate the top end.

8. The segmented rod assembly as recited in claim 7, wherein the tang is arranged adjacent to the outer surface.

9. The segmented rod assembly as recited in claim 1, wherein the plurality of segments further comprise a third segment arranged to be connected to a third vertebra of the spine.

10. The segmented rod assembly as recited in claim 9, wherein:
the first body includes a first outer surface and the at least one tang comprises a first tang;

the second segment further comprises a second tang extending from the second body, the second body includes a second outer surface, and the at least one channel comprises a first channel; and, the third segment comprises a third body including a third outer surface and a third channel arranged to engage with the second tang.

11. The segmented rod assembly as recited in claim 10, wherein the at least one tensioning member comprises:
 a first tensioning member extending at least partially through the first segment and the second segment; and,
 a second tensioning member extending at least partially through the second segment and the third segment.

12. The segmented rod assembly as recited in claim 11, further comprising:
 a first biasing element connected to the first tensioning member and operatively arranged to pull the first segment and the second segment together; and,
 a second biasing element connected to the second tensioning member and operatively arranged to pull the second segment and the third segment together.

13. The segmented rod assembly as recited in claim 1, wherein the at least one tensioning member comprises one or more muscle wires.

14. The segmented rod assembly as recited in claim 2, wherein the biasing element is operatively arranged to be controlled wirelessly.

15. A segmented rod assembly for aligning a spine including a plurality of vertebrae, comprising:
 a rod, including:
  a plurality of segments, the plurality of segments comprising at least:
   a first segment arranged to be connected to a first vertebra of the spine;
   a second segment arranged to be connected to a second vertebra of the spine; and,
   a third segment arranged to be connected to a third vertebra of the spine;
  a first tensioning member arranged at least partially within the first segment and the second segment; and,
  a second tensioning member arranged at least partially within the second segment and the third segment;
  wherein the first tensioning member and the second tensioning member are operatively arranged to be independently tensioned.

16. The segmented rod assembly as recited in claim 15, wherein:
 at least one segment of the plurality of segments comprises:
  a first body including a first outer surface; and,
  at least one tang extending from the first body and aligned with the first outer surface;
 an adjacent segment to the at least one segment comprises:
  a second body including a second outer surface; and,
  at least one channel arranged in the second outer surface; and,
 the at least one tang is operatively arranged to engage the at least one channel.

17. The segmented rod assembly as recited in claim 15, further comprising:
 a first biasing element connected to the first tensioning member; and,
 a second biasing element connected to the second tensioning member, wherein the first and second biasing elements are operatively arranged to pull the plurality of segments together.

18. The segmented rod assembly as recited in claim 17, wherein the first biasing element and the second biasing element are controlled remotely and independently of each other.

19. The segmented rod assembly as recited in claim 15, wherein:
 in a fully engaged state, the plurality of segments are rigidly connected with each other; and,
 in a partially engaged or relaxed state, the plurality of segments are at least partially spaced apart from each other.

20. A segmented rod assembly for aligning a spine including a plurality of vertebrae, comprising:
 a rod, including a plurality of segments, wherein:
  a first segment of the plurality of segments includes a protruding tang;
  a second segment of the plurality of segments includes a first end, a second end, a radially outward facing surface extending from the first end to the second end, the radially outward facing surface comprising a channel, the protruding tang is operatively arranged to engage the outward facing channel to rigidly connect the first and second segments; and,
  at least one segment of the plurality of segments is connected to a first vertebra of the spine; and,
 at least one tensioning member arranged at least partially within the plurality of segments, wherein the at least one tensioning member is operatively arranged to force the plurality of segments into engagement.

* * * * *